(12) United States Patent
Ho

(10) Patent No.: US 8,145,432 B2
(45) Date of Patent: Mar. 27, 2012

(54) SYSTEM OF BINDING STRUCTURE FOR POLYMER MOLECULE

(75) Inventor: Shirun Ho, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1464 days.

(21) Appl. No.: 11/657,090

(22) Filed: Jan. 24, 2007

(65) Prior Publication Data

US 2007/0260795 A1 Nov. 8, 2007

(30) Foreign Application Priority Data

Feb. 17, 2006 (JP) ................................. 2006-040685

(51) Int. Cl.
*G01N 33/48* (2006.01)
*G06F 17/50* (2006.01)
(52) U.S. Cl. ............................................ 702/19; 703/1
(58) Field of Classification Search ........................ None
See application file for complete search history.

(56) References Cited

OTHER PUBLICATIONS

Maier et al., A Discrete-Continuous Algorithm for Molecular Energy Minimization, IEEE, 1992, pp. 778-786.*

* cited by examiner

*Primary Examiner* — Jason Sims
(74) *Attorney, Agent, or Firm* — Stites & Harbison, PLLC; Juan Carlos A. Marquez, Esq.

(57) ABSTRACT

A simulation system that increases a polymer molecule binding prediction speed on a parallel and distributed computer system is provided. The simulation system determines a decomposition width that decomposes a search region of polymer molecule by means of translational operation and rotational operation and the number of searches in the decomposed regions into which the search region is decomposed, determines the number of decomposed regions into which the search region is decomposed, determines the number of computing units to which the decomposed regions are to be allocated, allocates the decomposed regions to the respective computing units, determines search points within the decomposed regions, transmits data of the search points to a computing unit that computes the binding energy and the energy gradient vector, performs communication control that receives data associated with the binding energy and the energy gradient vector from the computing unit, and determines the local minimum value of the binding energy in the decomposed region and the minimum value in the search region, thereby making it possible to determine the convergence of the binding energy.

20 Claims, 23 Drawing Sheets

SYSTEM OF BINDING STRUCTURE FOR POLYMER MOLECULE

CLAIM OF PRIORITY

The present application claims priority from Japanese Application JP 2006-040685 filed on Feb. 17, 2006, the content of which is hereby incorporated by reference into this application.

BACKGROUND OF THE INVENTION

The present invention relates to a system that predicts the binding of polymer molecule which is applied to a drug discovery simulation system as well as mass analysis that measures the interaction between biopolymers or an analysis system of protein chip. In order to increase the simulation computing speed and the analyzing speed of the above type, a parallel and distributed environment using a parallel and distributed computer system is effective, and the present invention is useful in a single computer.

In the post-genome age, there has been developed a compound molecular structure as a drug that promotes or inhibits the vital function of polymer molecule for protein, DNA and RNA which are obtained from genome information. For example, the molecular species, the reactive group, or the skeleton structure of a compound is changed to design the compound molecular structure so as to enhance the binding strength of protein with respect to target protein. In the drug discovery simulation system, a binding energy is computed with respect to a large number of configuration structures of protein and compound. The binding structure having the minimum binding energy is searched to perform the optimum design of the compound molecule structure. If the binding structure having the minimum binding energy of protein and compound can be searched in a high speed, it is possible to reduce a development period of the compound molecular structure with respect to target protein. Also, it is possible to reduce the costs that experimentally produce the compound molecule and measures the binding strength of the compound molecule and protein.

FIGS. 19 to 21 are diagrams showing a general structural example of a parallel and distributed computer system in which drug discovery simulation is performed under the parallel and distributed environments.

FIG. 19 shows a state in which each of computing units 1903 that are units of computing is made up of a computing processor unit 1901 that executes computing, and a memory unit 1902 that stores input data required to execute the computing or output data obtained by execution of the computing. Also, the computing units 1903 each of which is a unit of the computing are bound in a grid pattern by data transfer networks 1904 and 1905 that execute data transfer between the respective computing units 1903. One of the data transfer networks is connected with a personal computer 100 for control. The personal computer 100 executes the input of data to be subjected to simulation, the distribution of computation to the computing units 1903, and the tabulation of the computation results between the respective computing units 1903 and of the respective computing units 1903. Also, the system is provided with, for example, a management unit 1906 of the parallel and distributed computer system at a node between the personal computer 100 and the network. The management unit 1906 collects information on the number of processors $N_{PE}$ which can be operated by the entire system, the type of processor of the connectable computing units, or the speed of the network, and supplies the information to the personal computer 100.

FIG. 20 is a diagram showing a structural example in which the computing unit is formed of a cluster of personal computers, or a cluster 2001 of workstations, and structured by a data transfer network that is connected in a ring configuration by insernets 2002 that execute data transfer between the respective machines. Similarly, the insernet 2002 of the data transfer network is connected with the personal computer 100 for control. In this example, the personal computer 100 for control is connected to the insernet 2002 of the data transfer network. In this example, similarly, there is provided a management unit 2003 of the parallel and distributed computer system.

FIG. 21 is a diagram showing a structural example of a wide-area distributed environment in which the computing unit is made up of plural grid machines 2101 each having a parallel computer 2103, a cluster of personal computers, and a cluster 2001 of work stations connected to each other on a high-speed network 2002 that executes high-speed data transfer, and the respective grid machines 2101 are connected to each other in the ring manner on a high-speed network 2102. Similarly, in this case, the personal computer 100 for control is connected to a high-speed network 2102 of the data transfer network, and a management unit 2003 of a parallel and distributed computer system is disposed.

FIG. 22 is a conceptual diagram showing an example of a transacting function of a related system that performs simulation which predicts a binding structure of polymer molecule on the parallel and distributed computer system of the above type. Reference numeral 100 corresponds to the personal computer of the parallel and distributed computer system which is described with reference to FIGS. 19 to 21. The personal computer 100 includes an input system 101 for inputting simulation data by a user, a transaction and control unit 102 for executing a transaction for distributing the computation of a binding energy to the respective computing units 104 from the inputted data, and for executing a transaction for distributing the results of the computation of the binding energy to the respective computing units to integrate the computing results, and an output device 103 for displaying the operation status of the transaction and control unit 102 or the integrated data. Reference numeral 104 denotes the respective computing units of the parallel and distributed computer system that is described with reference to FIGS. 19 to 21, performs the calculation according to information given by the personal computer 100 for control, and reports the computation results to the personal computer 100. Also, reference numeral 105 denotes the management unit of the parallel and distributed computer system which is described with reference to FIGS. 19 to 21. The personal computers 100, the computing units 104, and the management unit 105 of the parallel and distributed computer system are indicated by dashed lines, and connected by heavy lines in the sense that the personal computers 100, the computing units 104, and the management unit 105 are capable of mutually interchanging necessary data with each other. Also, the association between the transaction step of the transaction and control unit 102 and the transaction step of the computing units 104 are connected by thin solid lines.

The user inputs search regions with respect to the binding structure of protein which is obtained from genome information and polymer molecule to be subjected to simulation such as DNA or RNA, for example, protein and compound in water molecule, as well as the number of decomposed regions which decompose the search region (Step 2211). Also, the user inputs the number of operable computing units $N_{PE}$ that distribute the computation of the decomposed regions that decompose the search region (Step 2212). In this example, the number of operable computing units $N_{PE}$ can be obtained by using data that is supplied from the management unit 105 of the parallel and distributed computer system, or can be obtained by designating a number that is smaller than the data from the input system 101 through the user. The output data of the respective computing units is the minimum binding energy of the binding structure of protein in water molecule, and the compound atomic coordinate data of protein and compound in water molecule in the binding structure. The output system 103 outputs the data as image or numeric data that is readily visible by the user, and displays the data on a display system.

A description will be given of a procedure of computing the binding energy and tabulating the computation results by means of the computing units of the parallel and distributed computer system. Reference numeral 2241 is a step of determining the number of decomposed regions that are distributed to the respective computing units by the aid of the number of decomposed regions that decompose the search region, and the number of computing units $N_{PE}$ that share the decomposed regions. Reference numeral 2242 is a step of determining the search points within the decomposed regions at which the binding energy is computed in the decomposed regions that are allocated to the respective computing units. Reference numeral 2243 is a step of communication control, which transmits data of the respective search points that are allocated for calculating the binding energy to the respective computing units that have been determined in Step 2241 and Step 2242. Also, on the contrary, the binding energies at the respective search points which have been calculated in the respective computing units are received. Reference numeral 2244 is a step of determining the minimum value among the local minimum values of the binding energies that have been computed in the respective computing units 104 which have been received in Step 2243, and the local minimum value that has been calculated in all of the computing units. Reference numeral 2245 is a step of determining whether the iterative calculation is executed, or not, on the basis of the convergence of the local minimum value of the binding energy within the decomposed region.

In the case of executing the iterative calculation, control is returned to Step 2242. In the case of completing the iterative calculation, the minimum value of the binding energy of protein and compound in water molecule, and the atomic coordinate data with respect to the binding structure are outputted to the output system 103.

A description will be given of a computing procedure using a Monte Carlo method in Step 2242 that computes the binding energy of protein and compound in the decomposed regions that have been allocated to the respective computing units with reference to FIG. 23. FIG. 23 is a conceptual diagram showing a binding energy in a search region of compound and protein due to translational operation or rotational operation. The binding energy has the complicated configuration of peaks and troughs according to the translational and rotational search regions. In the Monte Carlo method, a new configuration structure due to the translational operation and the rotational operation is formed by using random numbers on the basis of the arrangement position of the compound and protein and the binding energy, and the binding energy is computed. When a binding energy difference of the new arrangement position with respect to an original arrangement position is $\Delta E$, the probability P ($\Delta E$) of transiting to a new configuration structure is obtained on the basis of Expression (1).

$$P(\Delta E) = \exp(-\Delta E/k_B T) \qquad (1)$$

where $k_B$ is the Boltzmann coefficient, and T is an absolute temperature. Also, the number of searches until the configuration structure transits to the new configuration structure with the probability of $P_{th}$ is given by Expression (2).

$$F(\Delta E) = \frac{\log(1 - P_{th})}{\log\{1 - P(\Delta E)\}} \qquad (2)$$

BRIEF SUMMARY OF THE INVENTION

In the related system, the user inputs the search regions and the number of decomposed regions by which the search region is decomposed from the input system 101 with respect to protein that is obtained from the genome information and polymer molecule to be subjected to simulation such as DNA or RNA, and sets a decomposition width of the search region by the aid of the inputted number of decomposed regions. It is remarkably difficult for the user to determined the optimum decomposition width of the search region. When the decomposition width of the search region is too large, the binding energy in the search region has the configuration having a large number of peaks and troughs. As a result, the number of searches of Expression (2) which is represented by a difference of the binding energy increases. There is an issue that the number of searches is reduced without extremely increasing the decomposition width. On the other hand, when the division width of the search region is small, the number of decomposed regions increases. Since the number of searching the smaller decomposition regions depends on the number of peaks and troughs of the binding energy that is contained in the respective decomposed regions, and the difference in the binding energy, the number of searching the decomposed regions is not uniformly reduced. When the decomposition width of the search region is reduced without reason, the number of searches is increased according to the number of decomposed regions, and the decomposed regions that are large in the difference of the binding energy requires the large number of searches. Therefore, there is an issue that the number of searches is reduced without extremely decreasing the decomposition width.

It is estimated that the decomposition width that minimizes the number of searches exists in the decomposition widths of the search region, but it is impossible for the user to set the optimum decomposition width. In other words, in the related manner, the user has no other choice but to start to set the decomposition width from a decomposition width the user must think fit from the experience in using the system or the understanding of polymer molecule to be subjected to simulation, and to predict the appropriate decomposition width by the aid of the system while changing the decomposition widths by trial and error. An object of the present invention is to automatically set the decomposition width of the decomposed regions by the aid of a simulation system to increase the speed of computing the minimum value of the binding energy instead of setting the decomposition width by the user.

In order to achieve the above object, according to the present invention, there is provided a design system of a binding structure for polymer molecule that is useful in increasing the simulation speed of the binding structure of polymer molecule and the binding energy, which is applied to a drug discovery simulation system using a parallel and distributed computer system, as well as mass analysis that measures the interaction between biopolymers or an analysis system of protein chip.

The present invention is useful in a single computer as described above, but the following description will be given of a polymer molecule binding prediction simulation under a parallel and distributed environment.

In the present invention, the user is capable of implementing the polymer molecule prediction system by simply designating a search region for computing the binding energy of polymer molecules and the number of operable computing units $N_{PE}$ from an input system 101 of a personal computer 100 for control with respect to protein that is obtained from genome information and polymer molecule to be subjected to simulation such as DNA or RNA. To achieve the above object, a procedure of transacting the system is configured as follows.

In the personal computer 100 for control, (1) the decomposition width that decomposes the search region of polymer molecule, and the number of searches in the decomposed regions into which the search region is decomposed are determined.

(2) the number of decomposed regions by which the search region is decomposed is determined.

(3) the number of computing units to which the decomposed regions are to be allocated is determined.

(4) the decomposed regions are allocated to the respective computing units.

(5) the search points within the decomposed regions are determined.

(6) a communication is controlled in which the data of the search point is transmitted to the computing units on a parallel and distributed computer system that computes the binding energy and an energy gradient vector, and data of the binding energy and the energy gradient vector is received from the computing units.

(7) the local minimum values of the binding energies in the decomposed regions, and the minimum value in the search region are determined.

(8) the convergence of the binding energy is determined.

Also, in the respective computing units of the parallel and distributed computer system, (9) the binding energy and the energy gradient vector at the search point within the decomposed regions are computed from the data at the search point which is transmitted according to a transacting procedure 6 of the personal computer 100.

(10) the computation results are transmitted to the personal computer according to the transacting procedure 6 of the personal computer 100.

According to the present invention, it is necessary for the user to input the search region and the number of operable computing units, but it is unnecessary to set the decomposition width of the search region. The decomposition width of the search region can be automatically set by the design system of a binding structure for polymer molecule, and the number of decompositions of the search region is optimized with the result that the computing speed of the minimum value of the binding energy can be increased.

These and other objects and many of the attendant advantages of the invention will be readily appreciated as the same becomes better understood by reference to the following detailed description when considered in connection with the accompanying drawings.

DETAILED DESCRIPTION OF THE INVENTION

Now, a description will be given in more detail of preferred embodiments of the present invention with reference to the accompanying drawings.

In all of figures for explaining the embodiments, parts having the same functions are indicated by identical references, and their duplex description may be omitted.

(Basic Configuration of System)

Figure 19:
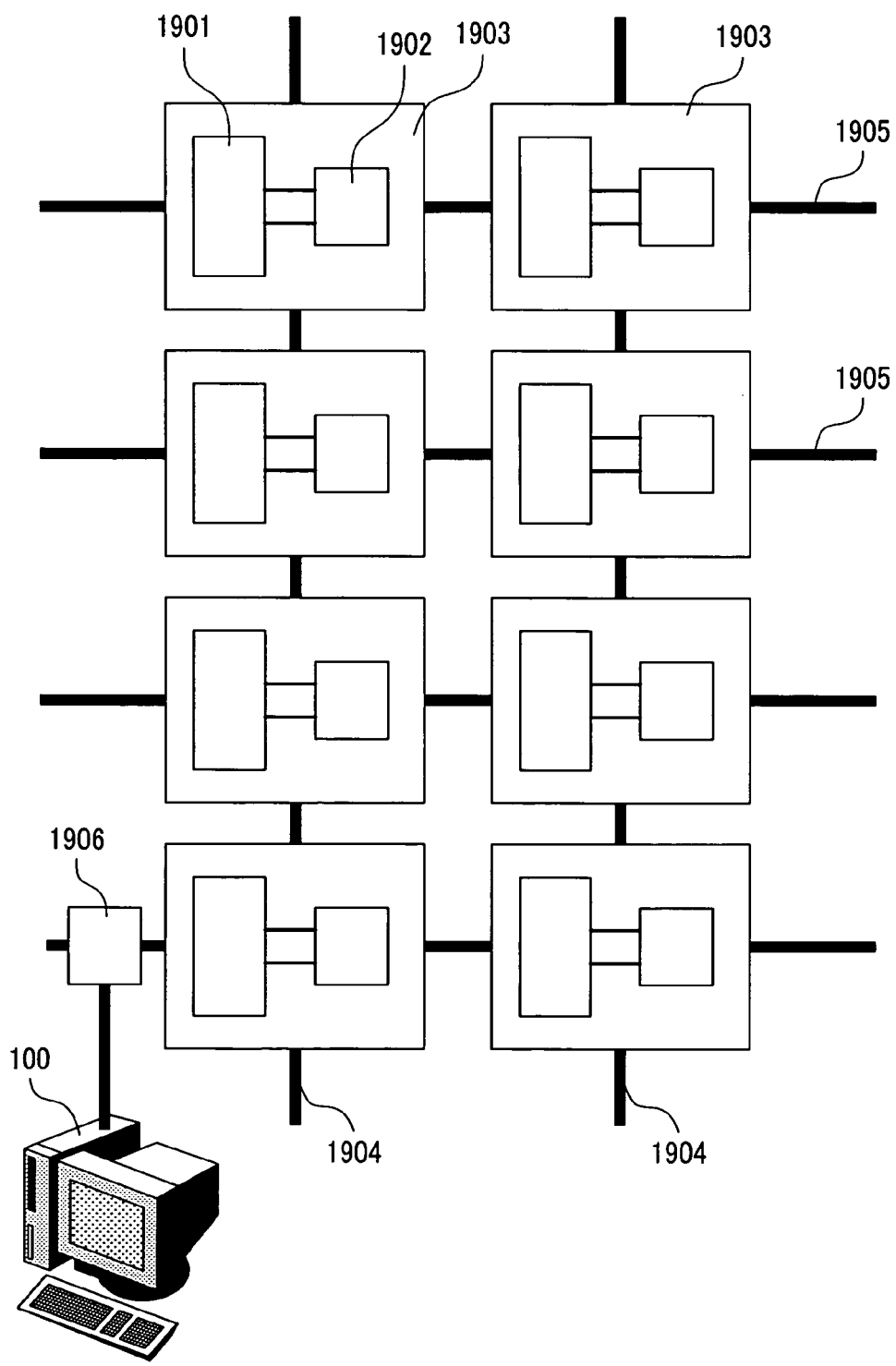
FIG. 19 is a diagram showing an example in which a data transfer network is of a grid configuration as one general structural example of the parallel and distributed computer system where drug discovery simulation is performed under a parallel and distributed environment.
Figure 20:
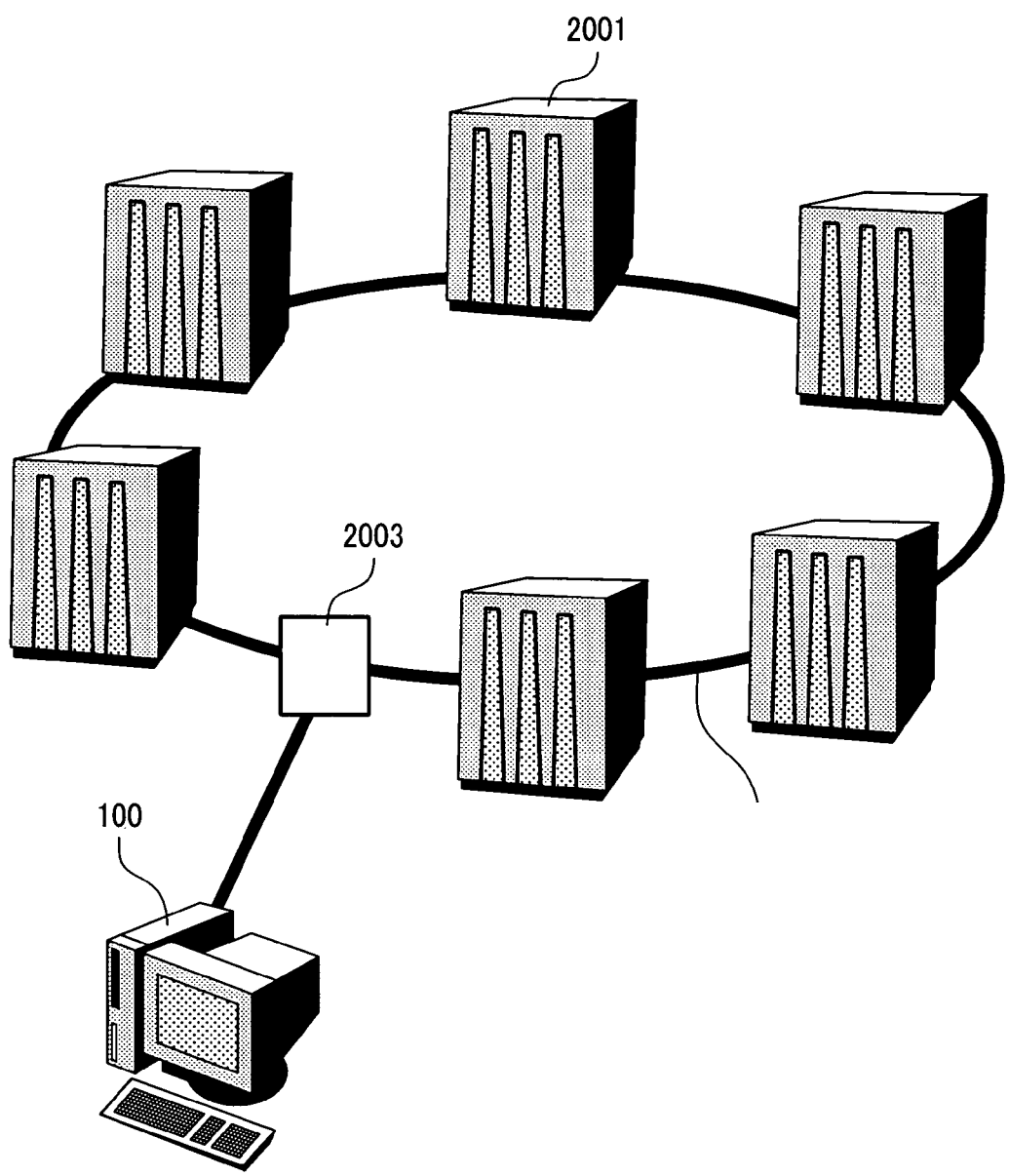
FIG. 20 is a diagram showing an example in which the data transfer networks are connected in a ring configuration.
Figure 21:
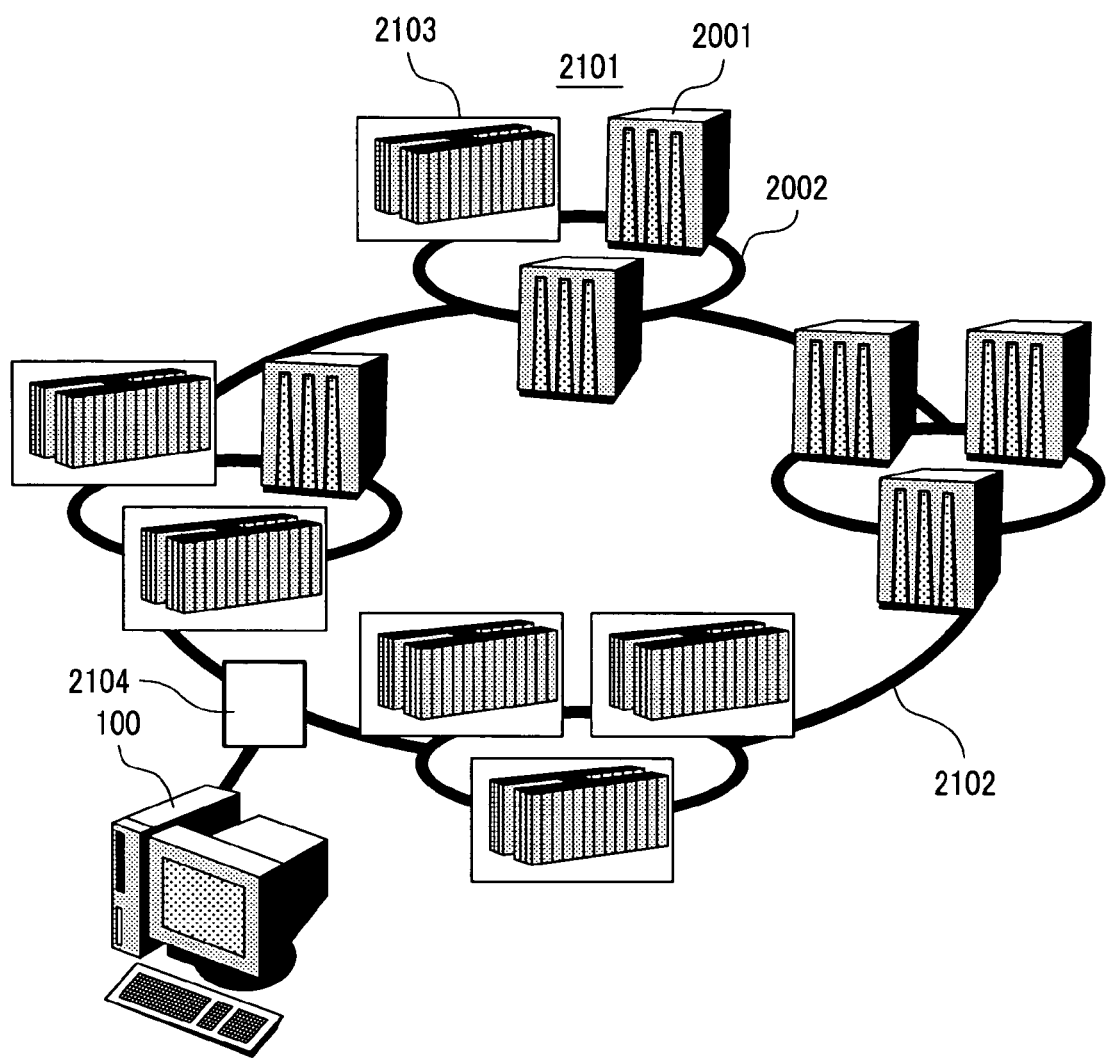
FIG. 21 is a diagram showing an example in which grid machines are connected to each other in a ring configuration on the data transfer network.
Figure 22:
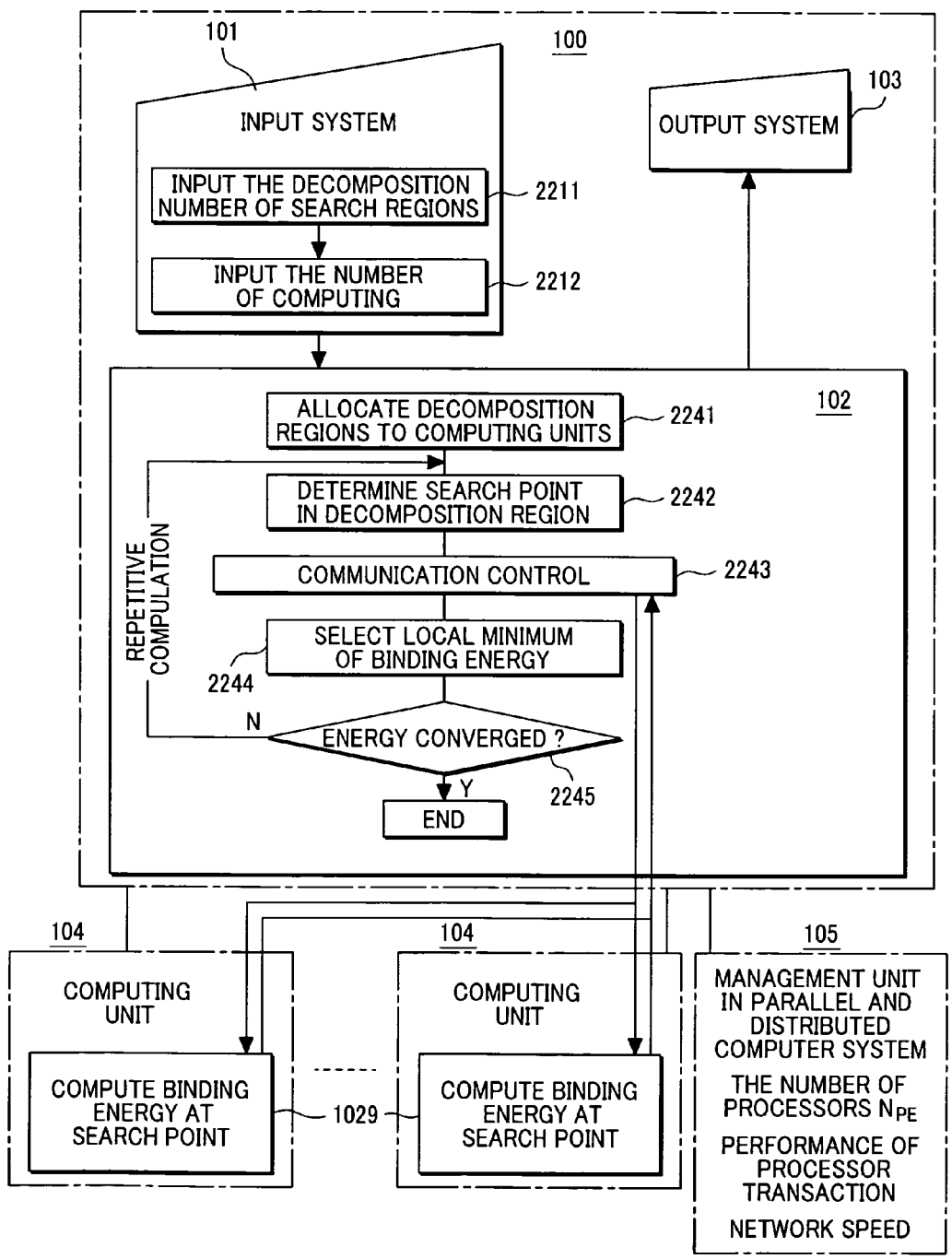
FIG. 22 is a diagram showing a concept that pays attention to an example of a transacting function of a related system that performs simulation which predicts a binding structure of polymer molecule on the parallel and distributed computer system.
Figure 23:
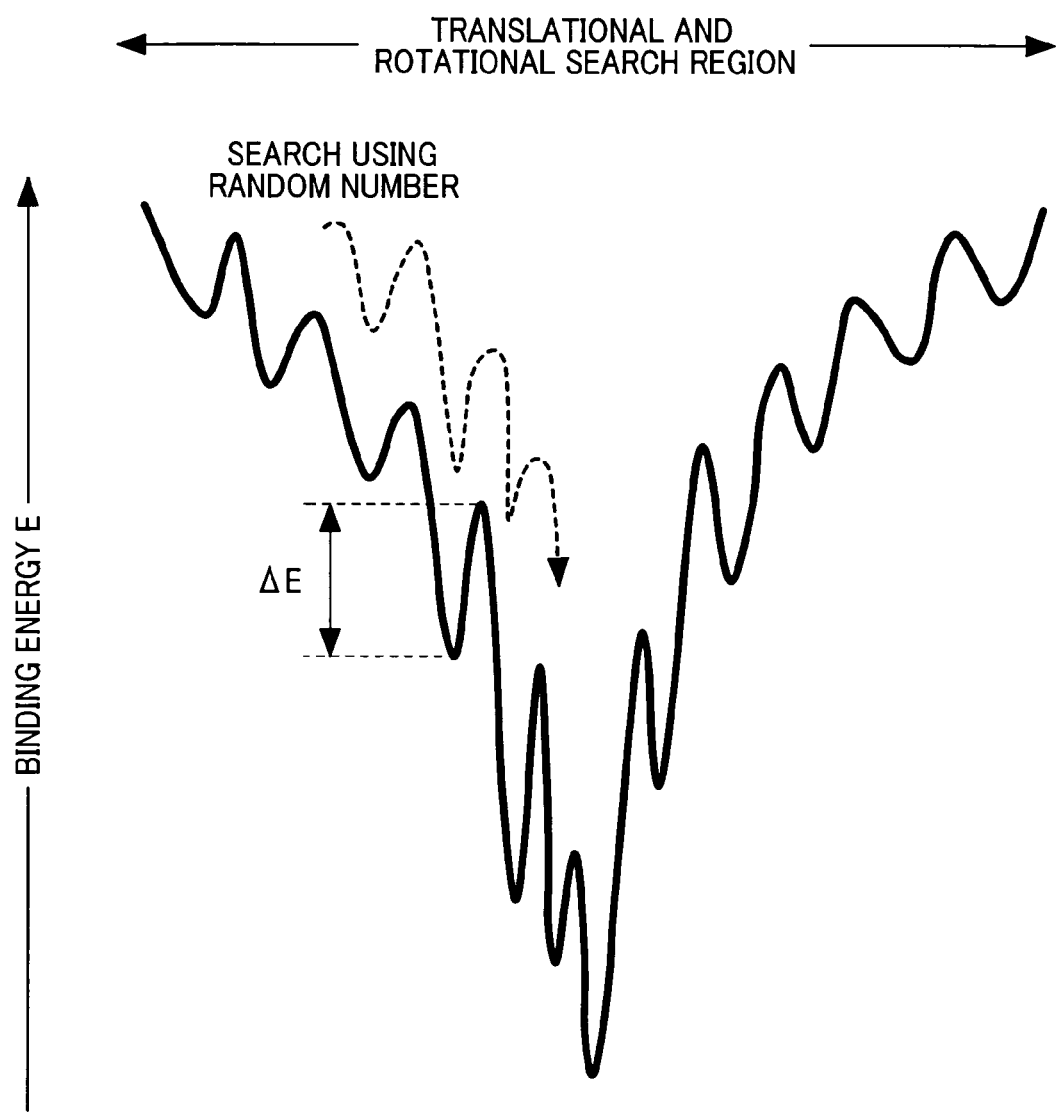
FIG. 23 is a diagram showing an example of the minimum search of a binding energy using a Monte Carlo method in a search region of translational operation and rotational operation.

FIGS. 19 to 21 show an example in which a parallel and distributed environment is structured by parallel computers and PC clusters, and the parallel computers and the PC clusters are controlled by a personal computer 100 as a general structural example of a parallel and distributed computer system. In a design system of a binding structure for polymer molecule according to the present invention, the configuration of a parallel and distributed computer system can be identical with the system configuration described above.

Figure 1:
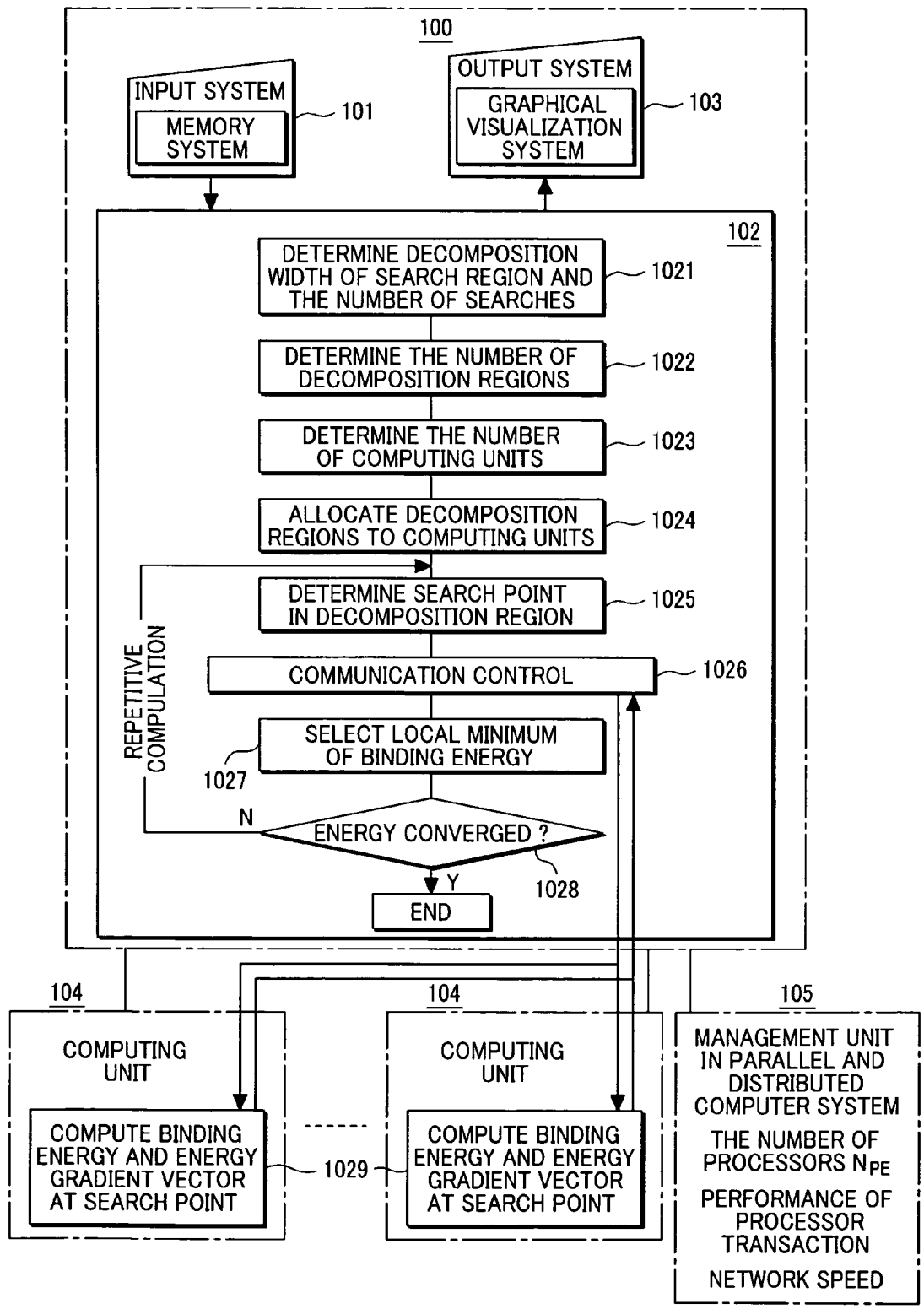
FIG. 1 is a conceptual diagram showing a basic structure of a design system of a binding structure for polymer molecule under a parallel and distributed environment according to the present invention.

FIG. 1 is a conceptual diagram showing a basic structure of a design system of a binding structure for polymer molecule according to the present invention. Referring to FIG. 1, reference numeral 100 denotes a personal computer for control of the design system of a binding structure for polymer molecule according to the present invention, which corresponds to the personal computer of the parallel and distributed computer system which is described with reference to FIGS. 19 to 21. The design system of a binding structure for polymer molecule includes an input system 101 for inputting data of simulation, a transaction and control unit 102 for executing a transaction for distributing the computation of a binding energy to the respective computing units 104 from inputted data, and for executing a transaction for integrating the results of distributing the computation to the respective computing units and computing the binding energy, and an output system 103 for displaying the operating status of the transaction and control unit 102 or the integrated data. In this example, the personal computer 100 includes a memory system such as a disk or a memory for holding necessary program or data, or a graphical visualization system that generates a display image for an interface with the user. However, for convenience, the memory system and the graphical visualization system is indicated in blocks of the input system 101 and the output system 103. Reference numeral 104 denotes the respective computing units of the parallel and distributed computer system which is described with reference to FIGS. 19 to 21, and executes computation according to information obtained from the personal computer 100 for control, and reports the computation results to the personal computer 100. Also, reference numeral 105 denotes a management unit of the parallel and distributed computer system described with reference to FIGS. 19 to 21. The personal computer 100, the computing units 104, and the management unit 105 of the parallel and distributed computer system are indicated by dashed lines, and connected by heavy lines in the sense that the personal computers 100, the computing units 104, and the management unit 105 are capable of mutually interchanging necessary data with each other. Also, the association between the transaction step of the transaction and control unit 102 and the transaction step of the computing units 104 are connected to each other by thin solid lines.

The user inputs, from the input system 101, search regions with respect to the binding structure of protein which is obtained from genome information and polymer molecule to be subjected to simulation such as DNA or RNA, for example, protein and compound in water molecule, as well as the number of operable computing units in the parallel computers and the PC clusters under the parallel and distributed environment.

In the transaction and control unit 102, the data to be subjected to simulation which is introduced through the input system 101 is inputted, and held in the memory system. Also, data for calculation of the binding energy is distributed to the computing units 104 through the above-described procedures (1) to (6). The computation results of the binding energy which have been performed through the above-described procedures (9) and (10) are integrated through the above procedures (6) to (8) on the basis of the data that has been distributed by the respective computing units 104, and then displayed on the output system 103.

Output data output the minimum binding energy with respect to the binding structure of protein and compound in water molecule, and atomic coordinate data of protein, compound, and water molecule in the binding structure.

Also, one of the computing units 104 acts as the transaction and control unit 102, and is capable of distributing the computation of the binding energy to the respective computing units 104, and integrating the computation results of the binding energy which has been performed by the respective computing units.

Hereinafter, a description will be given of a transaction procedure of distributing the computation of the binding energy to the respective computing units in the transaction and control unit 102 of the personal computer 100, and integrating the computation results. Reference numeral 1021 is a step of determining the decomposition width that decomposes the search region, and the number of searches for computing the binding energy in a search region that expresses a range where the operation of changing the atomic coordinates of compound is performed. Reference numeral 1022 is a step of determining the number of the decomposed search region (hereinafter referred to as "decomposed regions") and the range of the decomposed regions. Reference numeral 1023 is a step of determining the number of computing units in the parallel and distributed environment where the decomposed regions are allocated, by using the number of decomposed regions. Reference numeral 1024 is a step of determining the number of decomposed regions that are allocated to the respective computing units and the decomposed regions by using the number of decomposed regions, the number of searches, and the number of computing units in the parallel and distributed environment for allocation of the decomposed regions. Reference numeral 1025 is a step of determining search points within the decomposed regions for computation of the binding energy in the decomposed regions that are allocated to the respective computing units. Reference numeral 1026 is a step of communication control, which transmits data of the respective search points that are allocated for computation of the binding energy to the respective computing units which are determined in Steps 1024 and 1025. On the contrary, the binding energies and the energy gradient vectors at the respective search points which have been calculated in the respective computing units are received. Reference numeral 1027 is a step of determining the minimum value from the local minimum values of the binding energies that have been received in Step 1026 and computed by the respective computing units and the local minimum value that has been computed by all of the computing units. Reference numeral 1028 is a step of determining whether the iterative calculation is executed, or not, on the basis of the convergence of the local minimum value of the binding energy within the decomposed region. In the determination, since the number of searches is known in advance as will be understood from embodiments to be described later, the iterative calculation may not be performed when the number of searches exceeds the known value.

In the case of executing the iterative calculation, control is returned to Step 1025. In the case of completing the repetitive calculation, the minimum value of the binding energy of protein and compound in water molecule and the atomic coordinate data with respect to the binding structure are transmitted to the output system 103.

In Step 1029, data of the search points are received from Step 1026, and the operation of changing the atomic coordinates of compound with respect to the designated search points is executed in the respective computing units 104 of the parallel and distributed computer system. The atomic coordinates of protein, the atomic coordinates of water molecule, and the atomic coordinates of compound which have been changed are inputted, and the binding energy of protein and compound and the energy gradient vector, that is, a force that is exerted on compound and a torque that is exerted on compound are computed and outputted. The binding energy, the force that is exerted on compound, and the torque that is exerted on compound which have been outputted are transmitted to the personal computer 100 in Step 1026 of communication control.

First Embodiment

Figure 2:
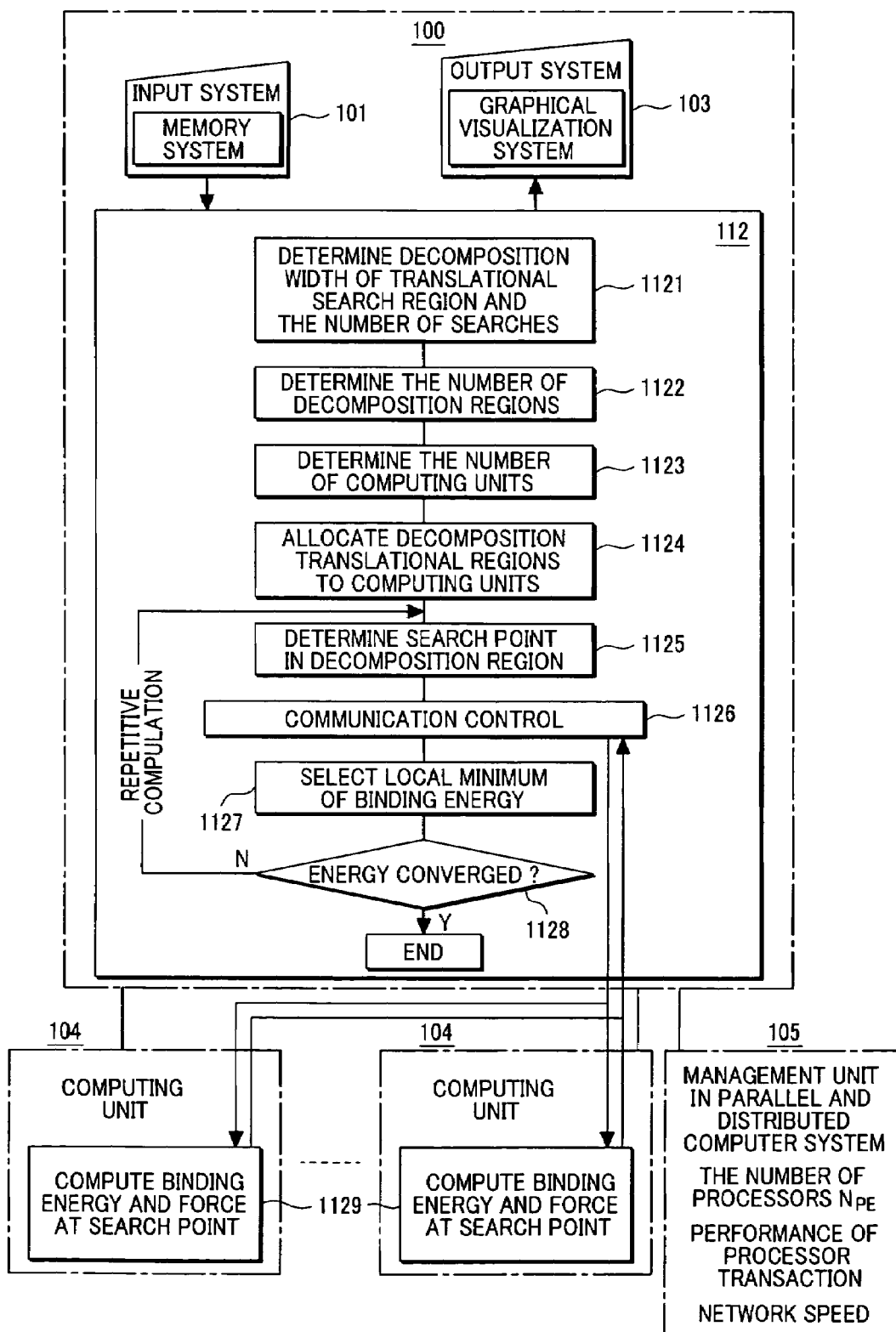
FIG. 2 is a conceptual diagram showing the configuration of a design system of a binding structure for polymer molecule according to a first embodiment of the present invention, and a diagram for explaining a specific transaction of a step of computing the minimum of a binding energy of protein by the aid of a translational operation of atomic coordinates of compound.

FIG. 2 is a conceptual diagram showing the configuration of a design system of a binding structure for polymer molecule according to a first embodiment of the present invention, and a diagram for explaining a specific transaction of a step of computing the minimum value of a binding energy of protein by the aid of a translational operation of atomic coordinates of compound. The entire configuration is identical with that shown in FIG. 1, but the transaction and control unit 102 and the respective transaction steps 1021 to 1029 shown in FIG. 1 are changed to the transaction and control unit 112 and the respective transaction steps 1121 to 1129 according to the changes of the transaction contents.

Figure 3:
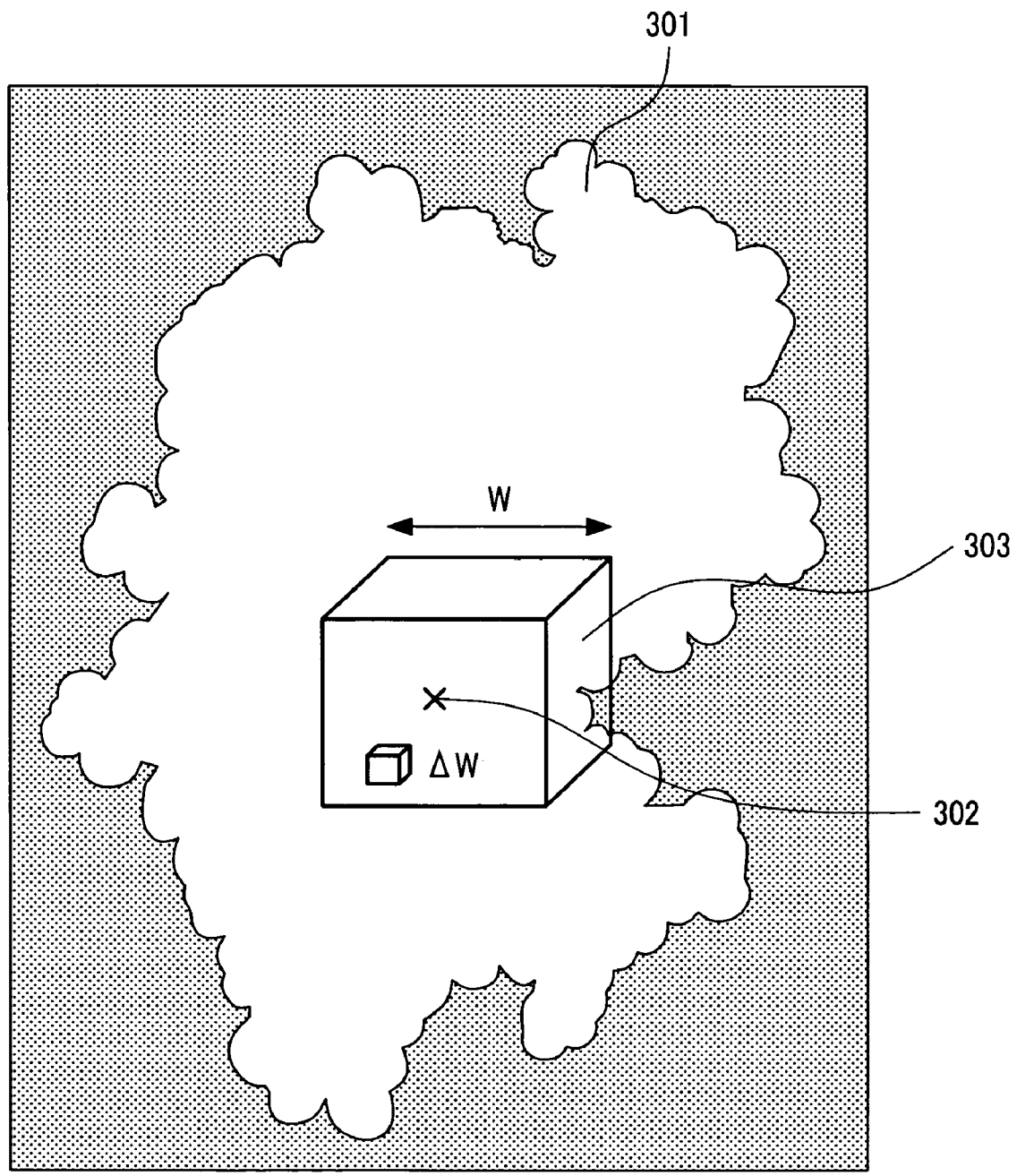
FIG. 3 is a diagram showing an example in which the search region using the translational operation is inputted with the coordinate values of the center position of the search region to display a spatial region which is a search region having a cubic configuration.

The user inputs a search region (hereinafter referred to as "translational search region") that expresses a range where the translational operation of the atomic coordinates of compound is performed from the input system 101 in order to search the minimum value of the binding energy of protein that is obtained from genome information and polymer molecule to be subjected to simulation such as DNA and RNA, for example, protein and compound in water molecule. As shown in an example of FIG. 3, the coordinate values of the center position 302 of the search region in protein 301, a spatial region width W303 that is a search region having a cubic configuration, and the number of available computing units $N_{pa}$ of the parallel computers or the PC clusters in the parallel and distributed environment are inputted. The number of available computing units $N_{pa}$ can be inputted by the user, or data that is supplied from the management unit 105 of the parallel and distributed computer system may be applied. In this example, a small cubic configuration $\Delta W$ indicated in the spatial region width W303 schematically shows a cube having a decomposition width $\Delta W$ of the translational search region which is determined according to a manner that will be described later.

In Step 1121, the decomposition width that minimizes the number of linearly searching the local minimum value of the binding energy and the number of line searches are determined in the translational search region that performs the translational operation of compound.

Figure 4:
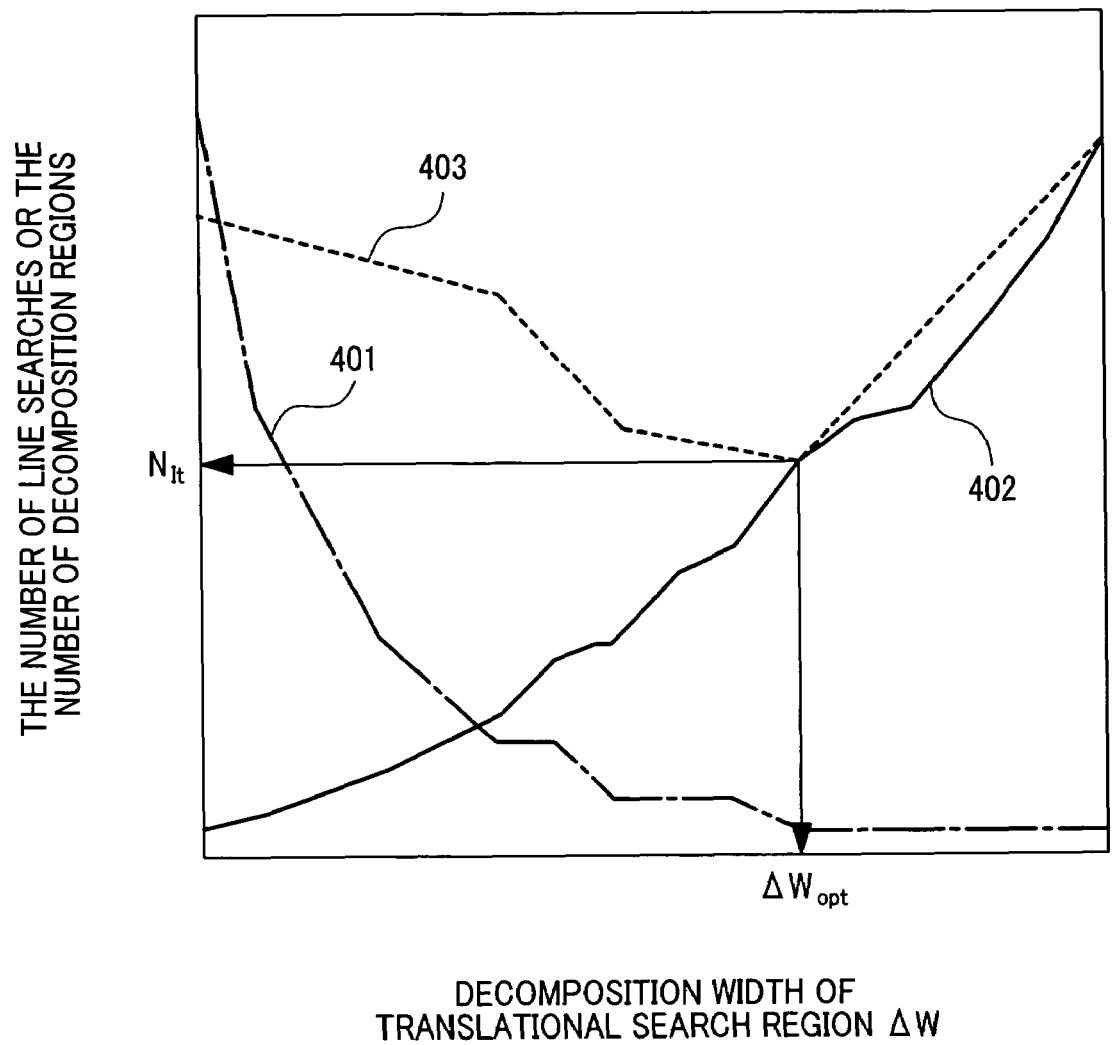
FIG. 4 is a diagram showing a change in decomposed transactional regions that are averagely allocated to the respective computing units with respect to the decomposition width, a change in the number of line searches with respect to the decomposition width, a change in the number of line searches of the local minimum value of the binding energy, and an optimum decomposition width with the axis of abscissa indicative of the decomposition width of the translational search region and the axis of ordinate indicative of the number of line searches or the number of decomposed regions.

FIG. 4 is a diagram showing a change in decomposed transactional regions (hereinafter referred to as "decomposed translational region) that are averagely allocated to the respective computing units with respect to the decomposition width, a change in the number of line searches with respect to the decomposition width, a change in the number of line searches of the local minimum value of the binding energy, and an optimum decomposition width with the axis of abscissa indicative of the decomposition width of the translational search region and the axis of ordinate indicative of the number of line searches or the number of decomposed regions (the number of decomposed search regions). Reference numeral 401 denotes a line that represents a change in the number of decomposed translational regions that are allocated to the respective computing units according to the decomposition width, reference numeral 402 denotes a line that represents a change of the number of line searches according to the decomposition width, and reference numeral 403 denotes a line that represents a change in the number of line searches of the local minimum value of the binding energy on the respective computing units according to the decomposition width. When the decomposition width of the translational search region is $\Delta W$, the number of decomposed translational regions that are averagely allocated to the respective computing units is $(W/\Delta W)^3/N_{pa}$. Also, in the respective decomposed translational regions, the binding energy is calculated by the line search in the energy gradient vector direction, that is, a direction of the force that is exerted on compound, the number of line searches until the local minimum value of the binding energy is found is given by F(X) represented in Expression (3). In this expression, $X=\Delta W/R_t$.

Figure 5:
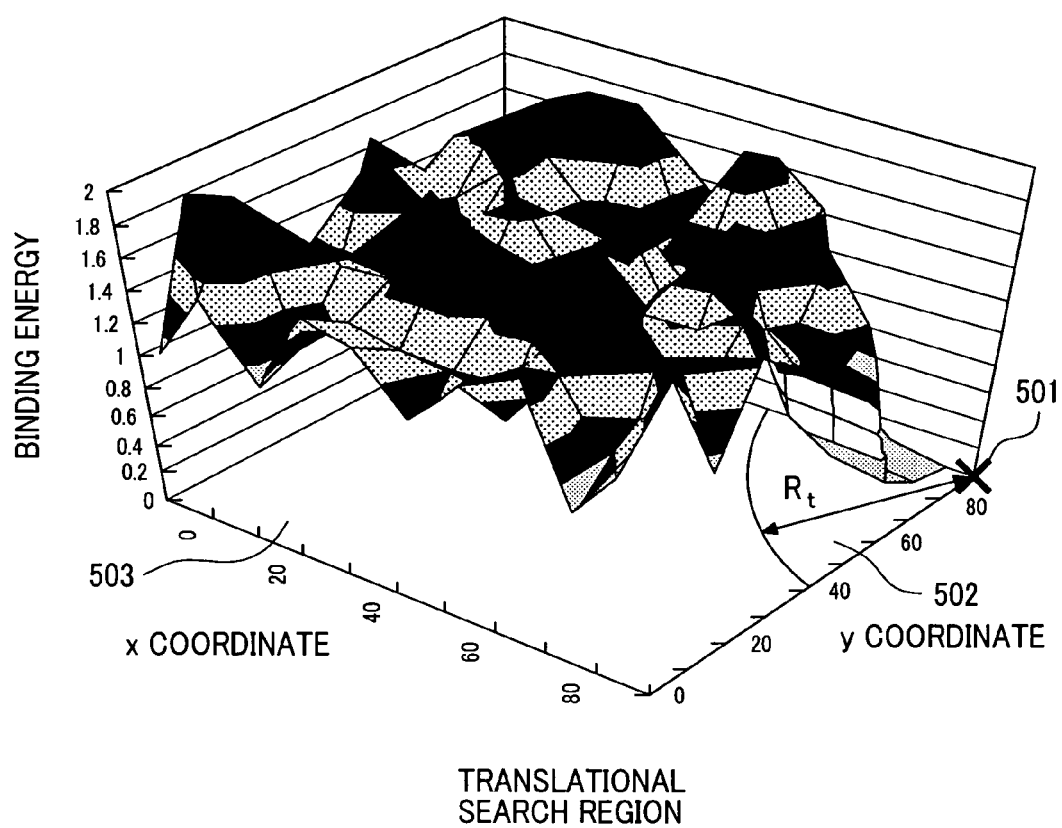
FIG. 5 is a diagram showing an example of a binding energy in a two-dimensional space of the decomposed translational search region.

FIG. 5 is a diagram showing an example of the binding energy in a two-dimensional space of the decomposed translational search region. When $R_t$ is within a distance of the radius $R_t$ from a coordinate position 501 at which the minimum value of the binding energy exists in the decomposed translational region, the binding energy is an energy region 502 of a quadratic function with respect to a distance, and when $R_t$ is equal to or higher than the radius $R_t$, the binding energy is a random energy region 503. The size of the radius $R_t$ can be prepared as the system, but can be inputted by the user.

A line 403 that represents a change in the number of line searches of the local minimum value of the binding energy on the respective computing units with respect to the decomposition width $\Delta W$ of the translational search region is represented by the product $(W/\Delta W)^3/N_{pa} \times F(\Delta W/R_t)$. Therefore, when the decomposition width $\Delta W_{opt}$ where $(W/\Delta W)^3/N_{pa} \times F(\Delta W/R_t)$ is the minimum is selected, the decomposition width $\Delta W_{opt}$ of the translational search region W as well as the binding energies on the respective computing units are computed, thereby making it possible to determine $N_{lt}=F(\Delta W_{opt}/R_t)$ where the number of line searches of the local minimum value of the binding energy is minimum.

Hereinafter, a description will be given of how to find the number of line searches F(X) for finding the local minimum value of the binding energy represented by Expression (3) with respect to X of a certain value with the probability $P_{th}$.

$$F(X) = \frac{\log(1 - P_{th})}{\log\{1 - P_1(X) - P_2(X)\}} \quad (3)$$

where $P_1(X)$ is given by Expression (4).

$$P_1(X) = \frac{1}{2\pi} \int_{\theta_3}^{\frac{\pi}{2}} d\theta \quad (4)$$

$$\cos^{-1}\left(\frac{x_{a1}x_{a2} + y_{a1}y_{a2} + z_{a1}z_{a2}}{\sqrt{x_{a1}^2 + y_{a1}^2 + z_{a1}^2}\sqrt{x_{a2}^2 + y_{a2}^2 + z_{a2}^2}}\right)$$

where $X_{ai}$, $Y_{ai}$, and $Z_{ai}$ (i=1, 2) are given by Expression (5) and $\theta_3$ is given by Expression (6).

$$\left.\begin{array}{l}x_{ai} = \alpha_i(\theta, X)(x_3 - x_i) + x_3 \\ y_{ai} = \alpha_i(\theta, X)(y_3 - y_i) + y_3 \\ z_{ai} = \alpha_i(\theta, X)(z_3 - z_i) + z_3\end{array}\right\} \quad (5)$$

$$\theta_3 = \cos^{-1}\left(\frac{z_3}{\sqrt{x_3^2 + y_3^2 + z_3^2}}\right) \quad (6)$$

where $a_i(\theta,X)$ is given by Expression (7), Expression (8), Expression (9), and Expression (10).

$$\alpha_i(\theta, X) = \frac{-b_i \pm \sqrt{b_i^2 - a_i c_i}}{a_i} \quad (7)$$

$$a_i = \{(x_3 - x_i)^2 + (y_3 - y_i)^2 + (z_3 - z_i)^2\}\cos^2\theta - (z_3 - z_i)^2 \quad (8)$$

$$b_i = \{x_3(x_3 - x_i) + (y_3 - y_i) + (z_3 - z_i)\}\cos^2\theta - z_3(z_3 - z_i) \quad (9)$$

$$c_i = \{x_3^2 + y_3^2 + z_3^2\}\cos^2\theta - z_3^2 \quad (10)$$

Also, $(x_1, y_1, z_1)$, $(x_2, y_2, z_2)$, and $(X_3, Y_3, Z_3)$ are given by Expression (11), Expression (12), and Expression (13).

$$(x_1, y_1, z_1) = \left(\sqrt{3X^2 - 2X + 1}, 0, 0\right) \quad (11)$$

$$(x_2, y_2, z_2) = \left(\frac{3X^2 - 2X}{\sqrt{3X^2 - 2X + 1}}, \sqrt{\frac{6X^2 - 4X + 1}{3X^2 - 2X + 1}}, 0\right) \quad (12)$$

$$(x_3, y_3, z_3) = \left(\frac{3X^2 - 2X}{\sqrt{3X^2 - 2X + 1}}, \frac{3X^2 - 2X}{\sqrt{6X^2 - 4X + 1}\sqrt{3X^2 - 2X + 1}}, \sqrt{\frac{9X^2 - 6X + 1}{6X^2 - 4X + 1}}\right) \quad (13)$$

On the other hand, $P_2(x)$ is given by Expression (14).

$$P_2(X) = \frac{3}{2\pi}\int_{\theta_1}^{\theta_2} 2\tan^{-1}\left(\frac{\sqrt{1 - 2B(\theta, X)^2}}{\sqrt{3X^2 - 4\beta(\theta, X)X + 2\beta(\theta, X)^2}}\right) \quad (14)$$

where $\beta(\theta, x)$ is given by Expression (15), Expression (16), Expression (17), and Expression (18).

$$\beta(\theta, X) = \frac{-b \pm \sqrt{b^2 - ac}}{a} \quad (15)$$

$$a = 2 - 2\cos^2\theta \quad (16)$$

-continued $$b = -X\{2 - 2\cos^2\theta\} \quad (17)$$

$$c = X^2\{2 - 3\cos^2\theta\} \quad (18)$$

where $\theta_1$ and $\theta_2$ are given by Expression (19) and Expression (20).

$$\cos\theta_1 = \frac{\sqrt{2X} - \frac{1}{\sqrt{2}}}{\sqrt{3X^2 - 2X + \frac{1}{2}}} \quad (19)$$

$$\cos\theta_2 = \frac{\sqrt{2X} - 1}{\sqrt{3X^2 - 2\sqrt{2}\,X + 1}} \quad (20)$$

In Step 1122, the number of decomposition of the translational search region and a range of the decomposed translational region are determined by the aid of the decomposition width $\Delta W_{opt}$ of the translational search region W. The number of translational regions by which the translational search region W is decomposed is $N_W = (W/\Delta W_{opt})^3$. When the translational coordinates within the decomposed translational region are (x, y, z), $0 = x = \Delta W_{opt}$, $0 = y = \Delta W_{opt}$, and $0 = z = \Delta W_{opt}$ are set as the decomposed translational region $W_1$, $0 = x = \Delta W_{opt}$, $0 = y = \Delta W_{opt}$, and $W_{opt} = z = 2\Delta W_{opt}$ are set as the decomposed translational region $W_2$, . . . , and $(W - \Delta W_{opt}) = x = W$, $(W - \Delta W_{opt}) = y = W$, and $(W - \Delta W_{opt}) = z = W$ are set as the decomposed translational region $W_{Nw}$.

In general, the decomposed translational region $W_n$ is represented by $(n_x - 1)\Delta W_{opt} = x = n_x \Delta W_{opt}$, $(n_y - 1)\Delta W_{opt} = y = n_y \Delta W_{opt}$, and $(n_z - 1)\Delta W_{opt} = z = n_z \Delta W_{opt}$, where $n = 1, 2, \ldots, N_w$, $n_x, n_y, n_z = 1, 2, \ldots, W/\Delta W_{opt}$.

As described above, the number of decomposed translational regions $N_w$, as well as the range of the decomposed translational regions $W_1, W_2, \ldots, W_n, \ldots, W_{Nw}$ can be determined.

In Step 1123, the number of computing units in the parallel and distributed environment for allocation of the decomposed translational regions by using the number of decomposed translational regions $N_w$. In the case where the number of decomposed translational regions $N_w$ is larger than the number of available computing units $N_{pa}$, the number of computing units $N_p$ to which the decomposed translational regions are allocated is $N_{pa}$. On the other hand, in the case where the number of decomposed translational regions $N_w$ is smaller than the number of available computing units $N_{pa}$, the number of computing units $N_p$ to which the decomposed translational regions are allocated is $N_w$. In this way, the number of computing units $N_p$ in the parallel and distributed environment for allocation of the decomposed translational regions can be determined.

In Step 1124, the number of decomposed translational regions that are allocated to the respective computing units and the decomposed translational regions are determined by using the number of decomposed translational regions $N_w$, the number of line searches $N_{lt}$ as well as the number of computing units $N_p$ in the parallel and distributed environment for allocation of the decomposed translational regions. Since the number of line searches with respect to the respective decomposed translational regions is $N_{lt}$, the number of decomposed translational regions that are allocated to the respective computing units can be substantially equalized, and the number $N_{di}$ of allocated decomposed translational regions is $[N_w/N_p]$ or $[N_w/N_p] - 1$. In this expression, a value obtained in the form of $[**]$ is rounded out to the whole number, and $N_{dt}$ decomposed translational regions that are arbitrarily selected from the decomposed translational regions $W_1, W_2, \ldots, W_{Nw}$ are allocated to each of the $N_p$ computing units under the parallel and distributed environment.

Figure 6A:
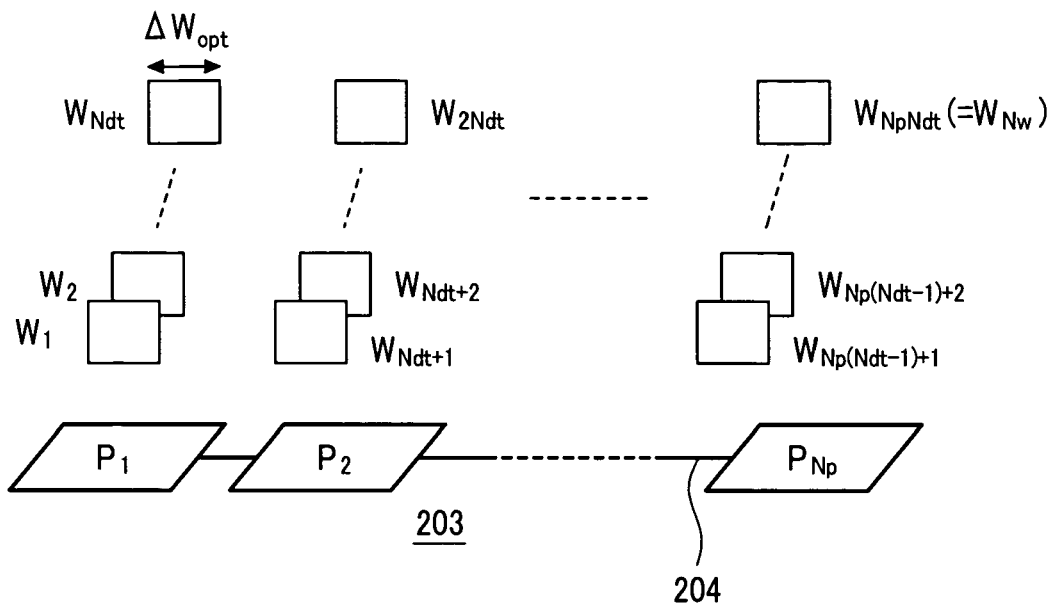
FIGS. 6A and 6B are diagrams for explaining an example of determining the number of decomposed translational regions that minimizes the number of line searches on the computing unit and the decomposed translational regions in the case where computing unit groups that are connected on the network have the same transaction performance and the different transaction performance, respectively.

FIG. 6A shows an appearance in which the decomposed translational regions $W_1, W_2, \ldots, W_{Ndt}$ are allocated to the computing unit $P_1$ of the computing units $P_1, P_2, \ldots, P_{NP}$ in the computer unit group 203 that is connected on the network 204, the decomposed translational regions $W_{Nd1+1}, W_{Ndt+2}, \ldots, W_{2Ndt}$ are allocated to the computing unit $P_2$, . . . , and the decomposed translational regions $W_{Np(Ndt-1)+1}, W_{Np(Ndt-1)+2}, \ldots, W_{NpNdt}$ $(=W_{Nw})$ are allocated to the computing unit $P_{Np}$. In general, the range of the decomposed translational region $W_n$ that is allocated to the computing unit $P_m$ is $(n_x - 1)\Delta W_{opt} = x = n_x \Delta W_{opt}$, $(n_y - 1)\Delta W_{opt} = y = n_y \Delta W_{opt}$, and $(n_z - 1)\Delta W_{opt} = z = n_z \Delta W_{opt}$, where $m = 1, 2, \ldots, N_p$, $n = 1, 2, \ldots$, and $N_w$, $n_x, n_y, n_z = 1, 2, \ldots, W/\Delta W_{opt}$.

Also, a description will be given of an example in which the number of decomposed translating regions that are allocated to the respective computing units, and the decomposed translational regions are determined in the case where the transaction performance of the computing units in the parallel and distributed computer system is different. In the parallel computers and the PC clusters under the parallel and distributed environment, the transaction performances $TP_1, TP_2, \ldots, TP_{N1}$ of the available computing units, and the number of computing units $N_{pa,1}, N_{pa,2}, \ldots, N_{pa,N1}$ are inputted from the input system 101, or applied with data that is obtained from the management unit 105 of the parallel and distributed computer system. In this example, $N_1$ is the type of available computing units.

In Step 1121 where the decomposition width that minimizes the number of line searches of the local minimum value of the binding energy, and the number of line searches are determined, $SN_{pa,i} \times \{T_{pi}/TP_{min}\}$ $(i=1, 2, \ldots, N_1)$ is applied instead of the above-mentioned number of available computing units $N_{pa}$. In this case, a value obtained in the form of $[**]$ is rounded out to the whole number, and $TP_{min}$ is the minimum transaction performance in the computing unit as a standard for conversion to the same transaction performance.

As described above, the number of decomposed translational regions $N_w$ is determined in Step 1122 with respect to the decomposition width $\Delta W_{opt}$ and the number of line searches $N_{lt}$ which are determined by converting the number $N_{pa}$ of available computing units to the equivalent number of computing units. Then, the number of computing units $N_p$ to which the decomposed translational regions are to be allocated is determined in Step 1123. In Step 1124, since the number of line searches with respect to the respective decomposed translational regions is $N_{lt}$, it is possible that the number of decomposed translational regions that are allocated to the respective computing units is substantially equalized.

The number of allocated decomposed translational regions $N_{dt,i} = [N_w/N_p] \times N_{pa,i} \times \{TP_i/TP_{min}\}$ $(i=1, 2, \ldots, N_1)$ is obtained by using the transaction performance of the respective computing units. $N_{di,i}$ decomposed translational regions that are arbitrarily selected from the decomposed translational regions $W_1, W_2, \ldots, W_{Nw}$ are allocated to each of the $N_i$ computing units in the parallel and distributed environment.

Figure 6B:
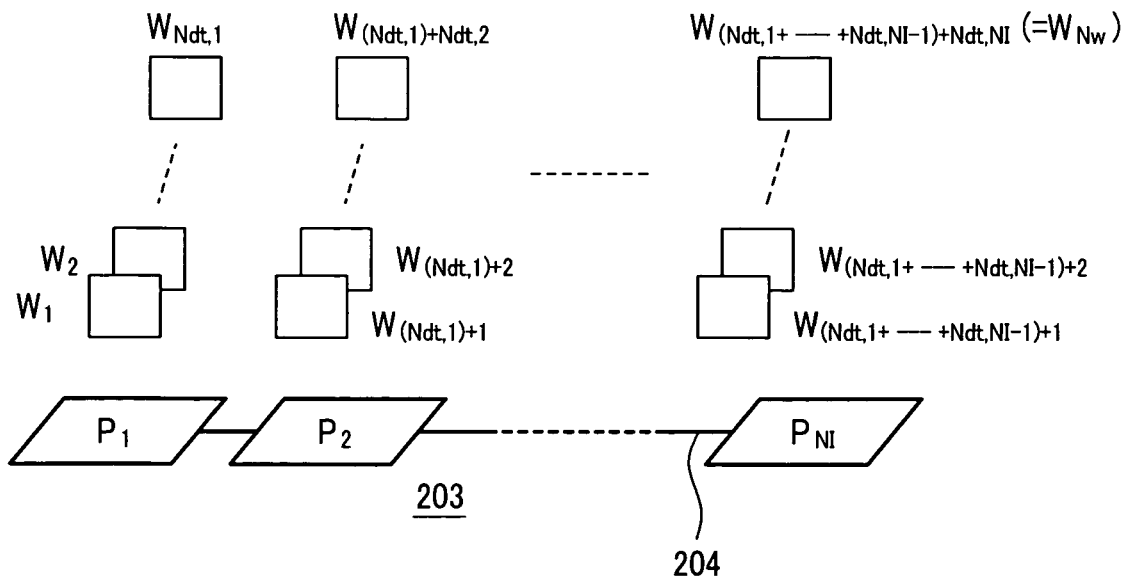

FIG. 6B shows an appearance in which the decomposed translational regions $W_1, W_2, \ldots, W_{Ndt,1}$ are allocated to the computing unit $P_1$ of the computing units $P_1, P_2, \ldots, P_{NP}$ in the computing unit group 203 that is connected on the network 204, the decomposed translational regions $W_{(Ndt,1)+1}, W_{(Ndt,1)+2}, \ldots, W_{(Ndt,1)+Ndt,2}$ are allocated to the computing unit $P_2, \ldots$, and the decomposed translational regions $W_{(Ndt,1+, \ldots, +Ndt,N1-1)+1}$, $W_{(Ndt,1+, \ldots +Ndt, N1-1)+2}, \ldots$, $W_{(Ndt,1+, \ldots, +Ndt, N1-1)+Ndt,N1}$ ($=W_{Nw}$) are allocated to the computing unit $P_{N1}$.

In Step 1125, the search point within the decomposed translational region where the binding energy is to be computed is determined in the decomposed translational regions $W_n$ that are allocated to the computing units.

Figure 7:
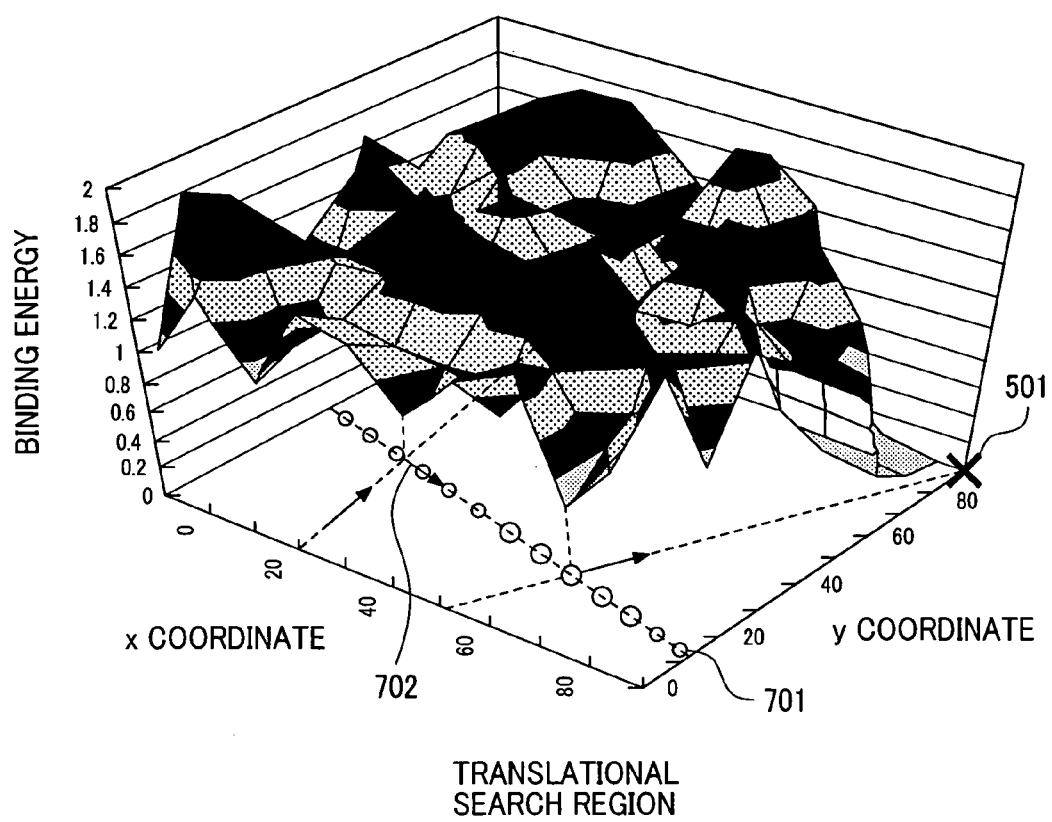
FIG. 7 is a diagram showing an example of the line search in an energy gradient direction in a decomposed search region of the two-dimensional space in the translational search region shown in FIG. 5.

FIG. 7 is a diagram showing an example of line search in the energy gradient direction in the decomposed search regions of the two-dimensional space of the translational search regions shown in FIG. 5. It is assumed that one of search points within the decomposed translational region $W_n$ is $(x_n, y_n, z_n)$. At the search point 701, it is assumed that a force norm 702 that is the gradient vector of the binding energy with respect to the translational coordinates is $F=(F_x, F_y, F_z)$. The search point within the decomposed translational region for computation of the binding energy is given by $(x_n \pm kF_x dw, y_n \pm kF_y dw, z_n \pm kF_z dw)$. In this expression, k is an integer that satisfies $(n_x-1)\Delta W_{opt}=x_n \pm kF_x dw=n_x \Delta W_{opt}$, $(n_y-1)\Delta W_{opt}=y_n \pm kF_y dw=n_y \Delta W_{opt}$, and $(n_z-1)\Delta W_{opt}=z_n \pm kF_z dw=n_z \Delta W_{opt}$. Also, dw is the translational width in the line search. Further, the translational width dw can be prepared at the system side as default, or can be set through the input system 101 by the user.

As described above, when it is assumed that the number of search points is $N_{It,n}$, $N_{It,n}$ search points $(x_n \pm kF_x dw, Y_n \pm kF_y dw, Z_n \pm kF_z dw)$ within the decomposed translational regions where the binding energy is to be computed can be determined with respect to the decomposed translational regions $W_n$ that have been allocated to the respective computing units.

Step 1126 is a communication control in which, in order to compute the binding energy, data of the search points that are allocated to the respective computing units which are determined in Step 1124 and Step 1125 is transmitted. When it is assumed that the decomposed translational regions $W_n$ are allocated to the computing units $P_m$ in Step 1124, and $N_{It,n}$ search points $(x_n \pm kF_x dw, y_n \pm kF_y dw, z_n \pm kF_z dw)$ which exist within the decomposed translational region $W_n$ are given in Step 1125, $N_{It,n}$ search points $(x_n \pm kF_x dw, y_n \pm kF_y dw, and z_n \pm kF_z dw)$ are transmitted to the computing unit $P_m$.

Figure 8:
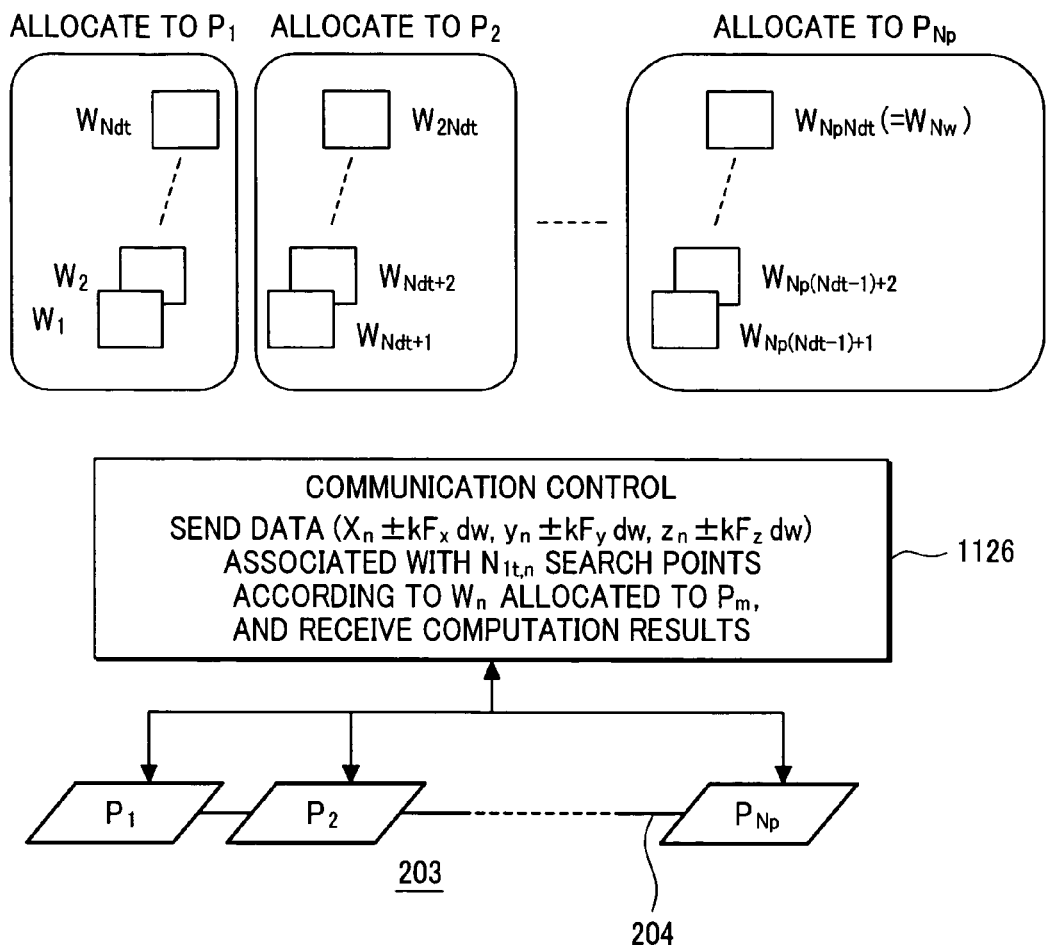
FIG. 8 is a diagram for explaining the transmission of the search point to the computing unit.

As shown in FIG. 8, data of $N_{It,n}$ search points $(x_n \pm kF_x dw, y_n \pm kF_y dw, and z_n \pm kF_z dw)$ that exist within the decomposed translational regions $W_n$ which are allocated to the respective computing units are transmitted to all of the computing units $P_1, P_2, \ldots, P_{Np}$ of the computing unit group 203. On the contrary, the binding energies with respect to the search points which have been computed by the respective computing units and the gradient vectors of the binding energy with respect to the translational coordinate, that is, a force that is exerted on compound is received. The binding energy of compound that has been subjected to translational operation and protein in water molecule, and a force that is exerted on compound are received with respect to $N_{It,n}$ translational coordinates $(x_n \pm kF_x dw, y_n \pm kF_y dw, and z_n \pm kF_z dw)$ which exist within the decomposed translational regions $W_n$ which have been transmitted to the computing units $P_m$.

In Step 1127, the minimum value is determined from the local minimum values of the binding energies that have been received in Step 1126 and computed by the respective computing units and the local minimum value that has been computed by all of the computing units. The search point that gives the smallest binding energy in $N_{It,n}$ binding energies is selected in correspondence with the $N_{It,n}$ search points $(x_n \pm kF_x dw, y_n \pm kF_y dw, and z_n \pm kF_z dw)$ which exist within the decomposed translational regions $W_n$ which have been computed by the computing units $P_m$. The line search repeats the iterative calculation that is $N_{It}$ times or more in the number of line searches.

The selected search point is a search point at which the gradient vector of the binding energy is obtained with respect to the translational coordinates described in Step 1125. The binding energy that has been obtained as the result of the iterative calculation is the local minimum value of the binding energies within the decomposed translational regions $W_n$. The smallest energy among the local minimum values of the binding energies that have been obtained in correspondence with all of the computing units $P_1, P_2, \ldots, P_{Nw}$ is the minimum value of the binding energy.

In Step 1128, it is determined whether the iterative calculation of the line search is repeated, or not, on the basis of the convergence of the local minimum values of the binding energy within the decomposed translational region. When the number of line searches of the decomposed translational region $W_n$ which have been allocated to the computing units $P_n$ is $N_{It}$ or lower, control is returned to Step 1125, and the iterative calculation of the line search is executed. When the number of line searches of the decomposed translational region $W_n$ which have been allocated to the computing units $P_n$ is equal to or higher than $N_{It}$, or when a difference between the local minimum value of the binding energy and the local minimum value of the binding energy which has been found in the previous iterative calculation is converged to a threshold energy or lower, the line search is completed. The minimum value of the binding energy of protein and compound in water molecule, as well as the atomic coordinate data with respect to the binding structure of protein and compound in water molecule is transmitted to the output system 103.

In Step 1129, the binding energy corresponding to the search point in the respective computing units, and the gradient vector of the binding energy with respect to the translational coordinates are calculated. The respective computing units $P_m$ receive the data of the search points, that is, $N_{It,n}$ translational coordinates $(x_n \pm kF_x dw, y_n \pm kF_y dw, and z_n \pm kF_z dw)$ within the decomposed translational regions $W_n$ from Step 1126. The respective computing units $P_m$ execute the translational operation with respect to the atomic coordinates of compound by using the search points $(x_n \pm kF_x dw, y_n \pm kF_y dw, and z_n \pm kF_z dw)$. The respective computing units Pm computes $N_{It,n}$ binding energies and a force that is exerted on compound from compound that has been subjected to translational operation, and the atomic coordinates of protein in water molecule. The binding energies corresponding to $N_{It,n}$ search points $(x_n \pm kF_x dw, y_n \pm kF_y dw, and z_n \pm kF_z dw)$ which exist within the decomposed translational regions $W_n$, and the force that is exerted on compound are transmitted to Step 1126.

A description will be given of a specific example in which the cubic configuration of the spatial region width W=6 Å in the translational search region is inputted from the input system 101 as the search region with respect to the binding structure of protein and compound in water molecule, and the number of available computing units $N_{pa}=60$ in the parallel and distributed computer system is inputted with reference to FIG. 9. In Step 1121, the decomposition width of the translational search region and the number of searches are determined.

Figure 9:
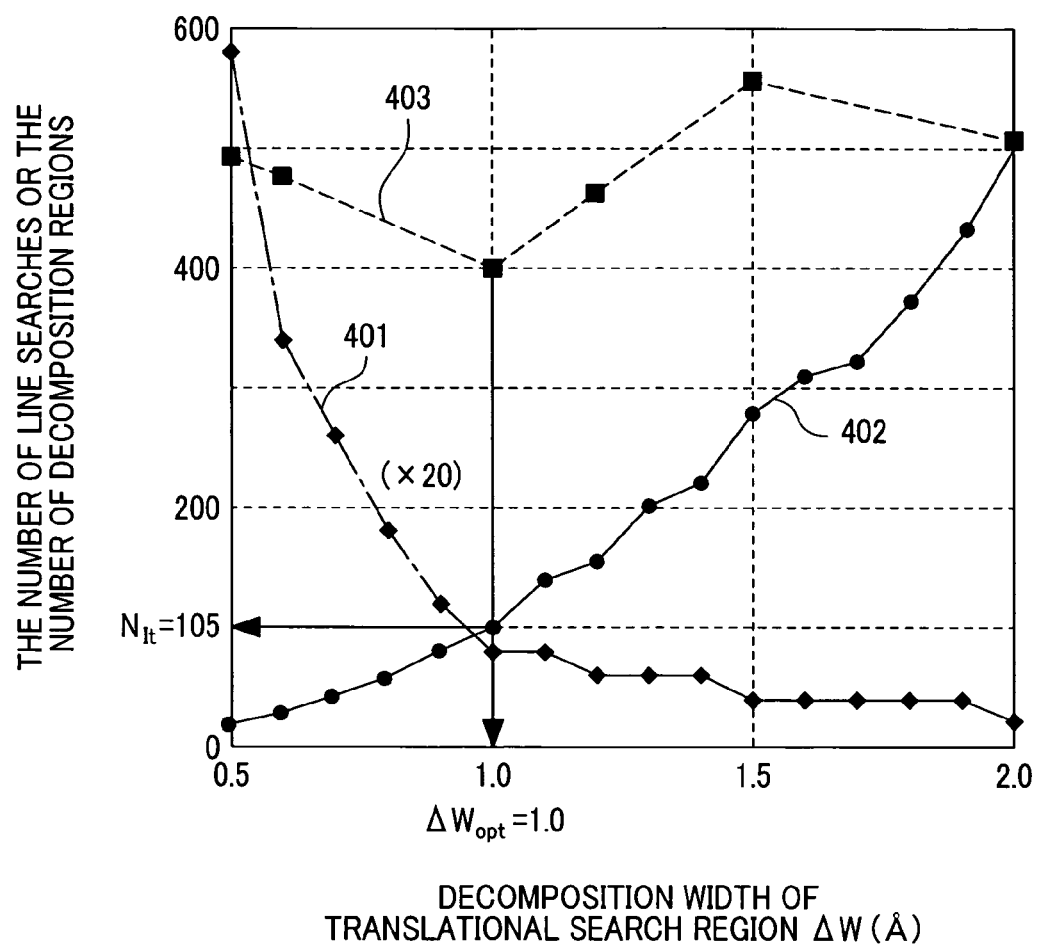
FIG. 9 is a diagram showing a change in decomposed transactional regions that are averagely allocated to the respective computing units with respect to the decomposition width, a change in the number of line searches with respect to the decomposition width, a change in the number of line searches of the local minimum value of the binding energy, and an optimum decomposition width with the axis of abscissa indicative of the decomposition width of the translational search region and the axis of ordinate indicative of the number of line searches or the number of decomposed regions.

FIG. 9 shows a change 401 in the number of decomposed translational regions (hereinafter, referred to as "the number of decomposed translational regions) which are averagely allocated to the respective computing units with respect to the decomposition width, a change in the number of line searches with respect to the decomposition width when $R_t$ is 0.5 Å, the number of line searches 403 that obtains the local minimum value of the binding energy on the respective computing units, and the optimum decomposition width with the axis of abscissa indicative of the decomposition width of the translational search region and the axis of ordinate indicative of the number of line searches or the number of decomposed regions as in FIG. 4. The decomposition width $\Delta W_{opt}$ of the translational search region where the number of line searches is the minimum on the respective computing units becomes 1 Å, and the number of line searches $N_{lt}$ can obtain 105.

Figure 10:
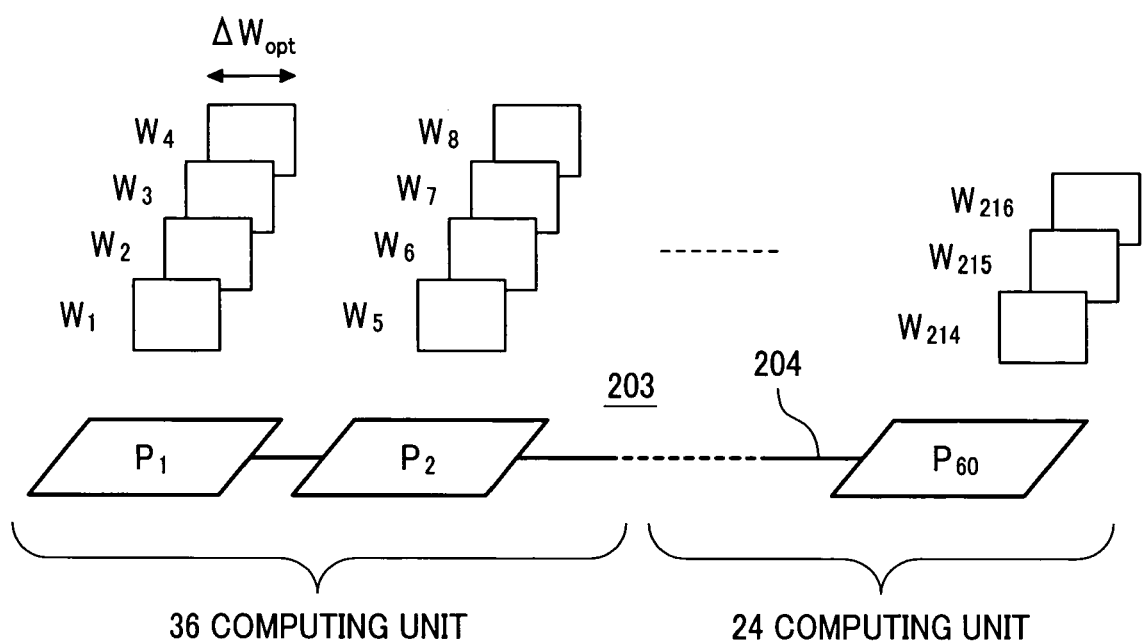
FIG. 10 is a diagram for explaining an example of determining the number of decomposed translational regions that minimize the number of line searches on the computing units of computing unit groups that are connected to each other on the network, and the decomposed translational regions.

In Step 1122, the number of decomposed translational regions $N_w=(W/\Delta W_{opt})^3$ is 216 by using the optimum decomposition width $\Delta W_{opt}=1$ Å. In Step 1123, since the number of decomposition regions $N_w=216$ is larger the number of available computing units $N_{pa}=60$, the number of computing units $N_p$ to which the decomposed translational regions are to be allocated is 60. In Step 1124, since the number of line searches $N_{lt}$ with respect to the respective decomposed translational regions is 105, the number of decomposed translational regions that are allocated to the respective computing units can be substantially equalized. For example, as shown in FIG. 10, the number of decomposed translational regions that are allocated to 36 computing units is distributed 4 by 4 with respect to the number of computing units $N_p=60$ of the computing unit group 203 that is connected on the network 204, and the number of decomposed translational regions $N_{dt-1}$ that are allocated to 24 computing units is distributed 3 by 3.

In Step 1125, the search points of line searches within the decomposed translational regions which have been allocated to the respective computing units are determined. Data of the search points of the line searches is transmitted to the respective computing units in Step 1126, and the binding energy corresponding to the search points in the respective computing units, and the gradient vectors of the binding energies with respect to the translational coordinates are computed and transmitted to Step 1126, in Step 1129. In Step 1127, the local minimum values of the binding energies that have been computed by the respective computing units are obtained. In Step 1128, the iterative calculation that is 105 in the number of line searches $N_{lt}$ is executed.

Figure 11:
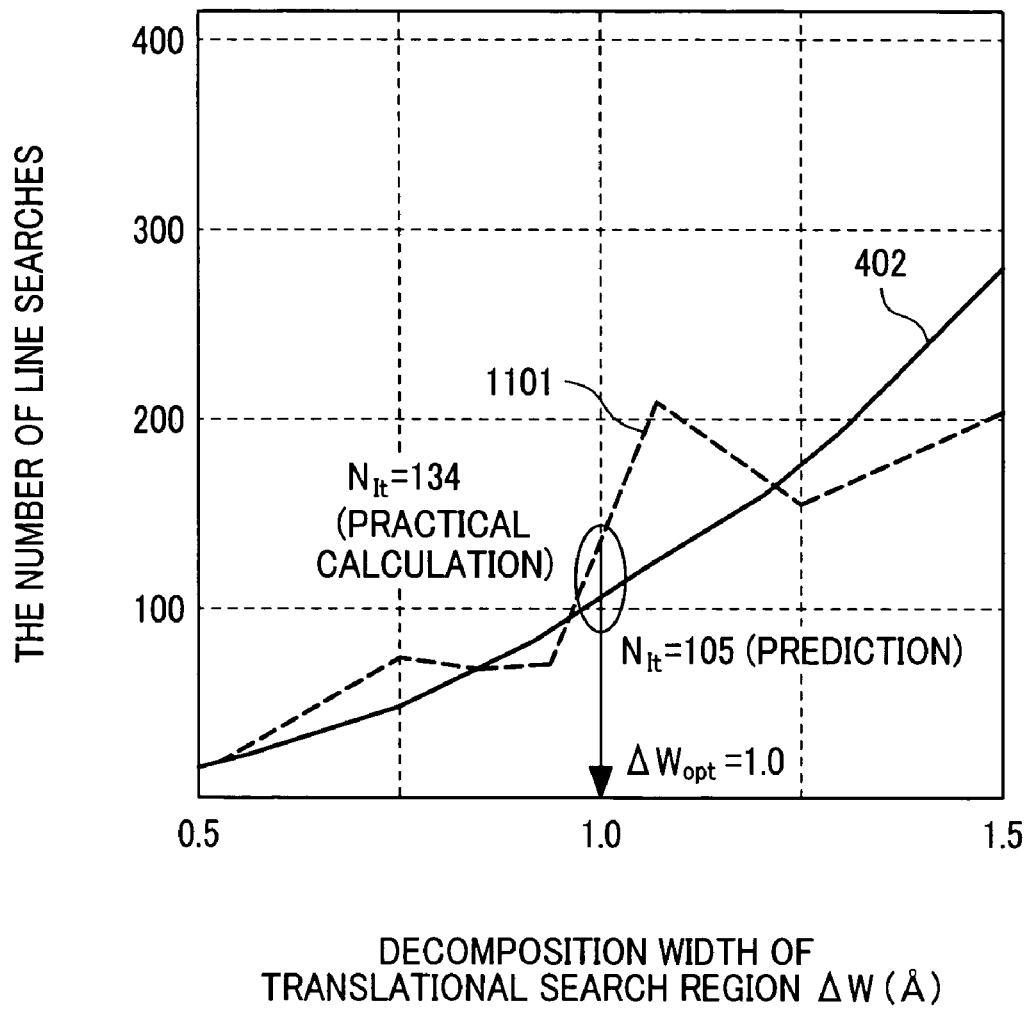
FIG. 11 is a diagram showing the number of line searches that minimize the local minimum value of the binding energy.

FIG. 11 is a diagram showing the number of line searches that obtain the local minimum values of the binding energy. A solid line 402 represents a predicted value that is obtained in Step 1121, and a dotted line 1101 is the computation results of the simulation according to the present invention. In the simulation, the average number of line searches that obtain the local minimum value of the binding energy in the decomposed translational region is 134, which relatively excellently coincides with the predicted value. The number of line searches on the respective computing units is a product of the number of line searches of the respective decomposed translational regions and the number of decomposed regions on the respective computing units, and therefore 420.

On the other hand, the number of line searches for obtaining the local minimum value of the binding energy when only one of the computing units is used is predicted as 4740 by the aid of Expressions (3) to (20). Therefore, the number of line searches that obtain the local minimum values of the binding energy is reduced down to $^{4740}/_{420}=^{1}/_{11}$ times by means of the design system of a binding structure for polymer molecule using the parallel and distributed computer system, thereby making it possible to compute the binding structure that minimizes the binding energy in a high speed. In other words, the user is capable of performing high-speed computation by merely setting the search region that represents a range where the translational operation of the atomic coordinates of polymer molecule to be subjected to simulation, and the number of available computing units $N_{pa}$ in the parallel computers or the PC cluster under the parallel and distributed environment.

Second Embodiment

Figure 12:
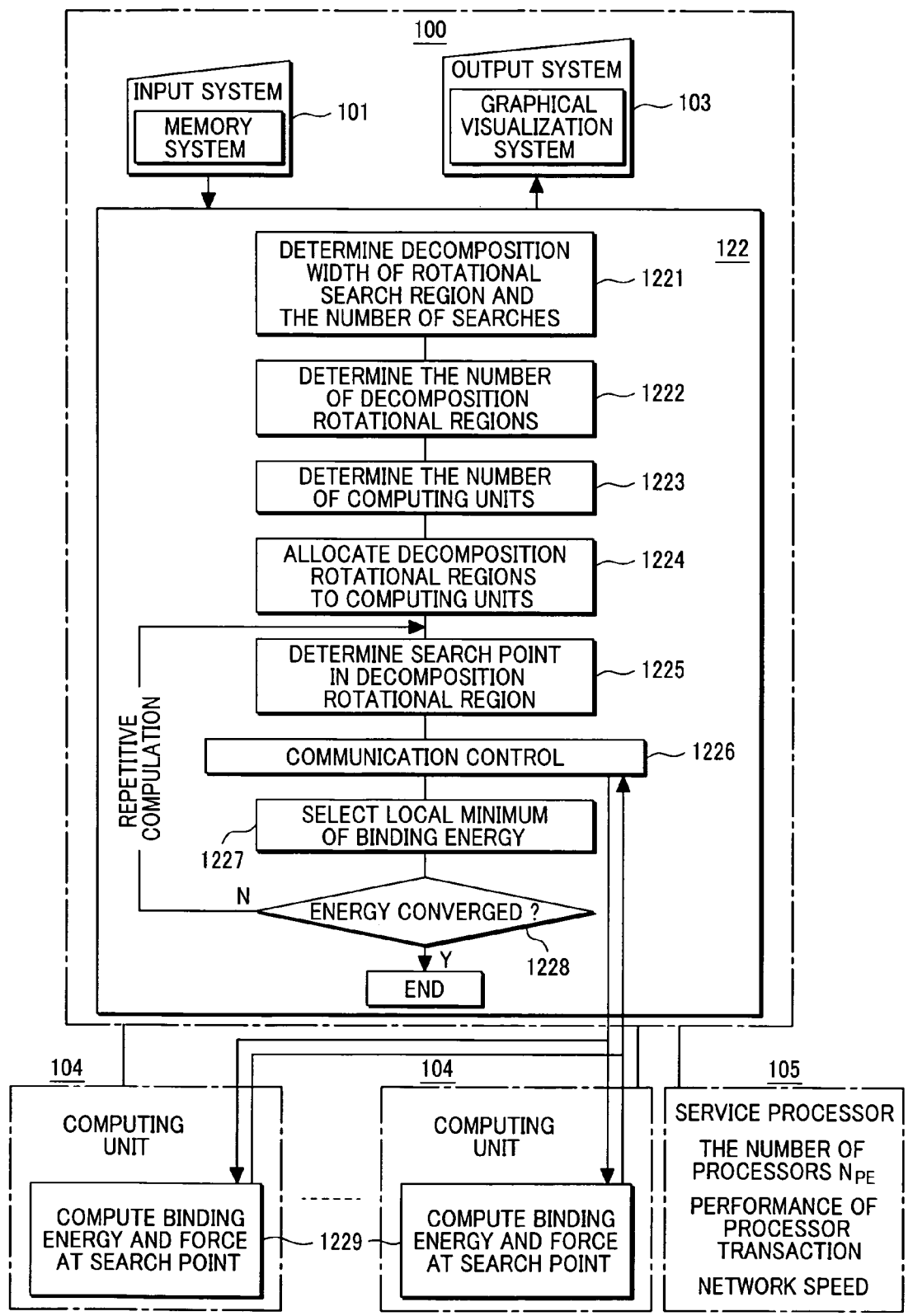
FIG. 12 is a conceptual diagram showing the configuration of a design system of a binding structure for polymer molecule according to a second embodiment of the present invention, and a diagram for explaining a specific transaction of a step of computing the minimum of a binding energy of protein by the aid of a rotational operation of compound.

FIG. 12 is a conceptual diagram showing the configuration of a design system of a binding structure for polymer molecule according to a second embodiment of the present invention, and a diagram for explaining a specific transaction of a step of computing the minimum value of a binding energy of protein by the aid of a rotational operation of compound whereas the first embodiment describes the transaction of computing the minimum value of the binding energy of protein by the aid of the translational operation of the atomic coordinates of compound. In this example, the entire configuration is identical with the configuration shown in FIG. 1 as in the first embodiment. However, the transaction and control unit 102 and the respective transaction steps 1021 to 1029 in FIG. 1 are changed to a transaction and control unit 122 and the respective transaction steps 1221 to 1229 according to the change of the processing contents.

Figures 13A, 13B, 13C:
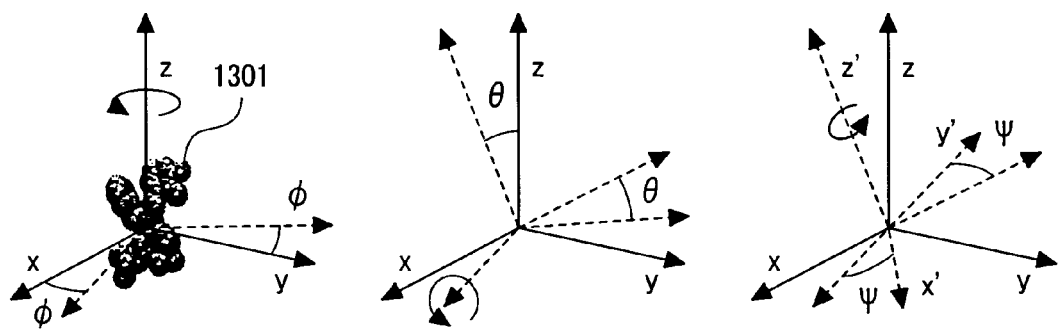
FIGS. 13A, 13B, and 13C are diagrams showing an example of search regions that perform the rotational operation of compound which is indicated by Euler's angles (F, θ, ψ)

The user inputs an angle region width x from the input system 101 as a search region (hereinafter referred to as "rotational search region") that expresses a range where the rotational operation of compound is performed in order to search the minimum value of the binding energy of protein that is obtained from genome information and polymer molecule to be subjected to simulation such as DNA and RNA, for example, protein and compound in water molecule. As shown in FIGS. 13A to 13C, the search region where the rotational operation of compound 1301 is performed is represented by $0=F=x$, $0=\theta=x/2$, and $0=\psi=x$ when being expressed by Euler's angles (F, θ, ψ), where F is the rotational angle about a z-axis, θ is the rotational angle about an x-axis subsequent to the rotation of the z-axis, and ψ is the rotational angle about the z-axis subsequent to the rotations of the z-axis and the x-axis, and x is $0=x=2p$. Also, the user inputs the number of computing units $N_{pa}$ in the parallel computers or the PC cluster in the parallel and distributed environment.

Hereinafter, a description will be given of a transaction flow of distributing the binding computation to the respective computing units and integrating the results in the transaction and control unit 122.

Figure 14:
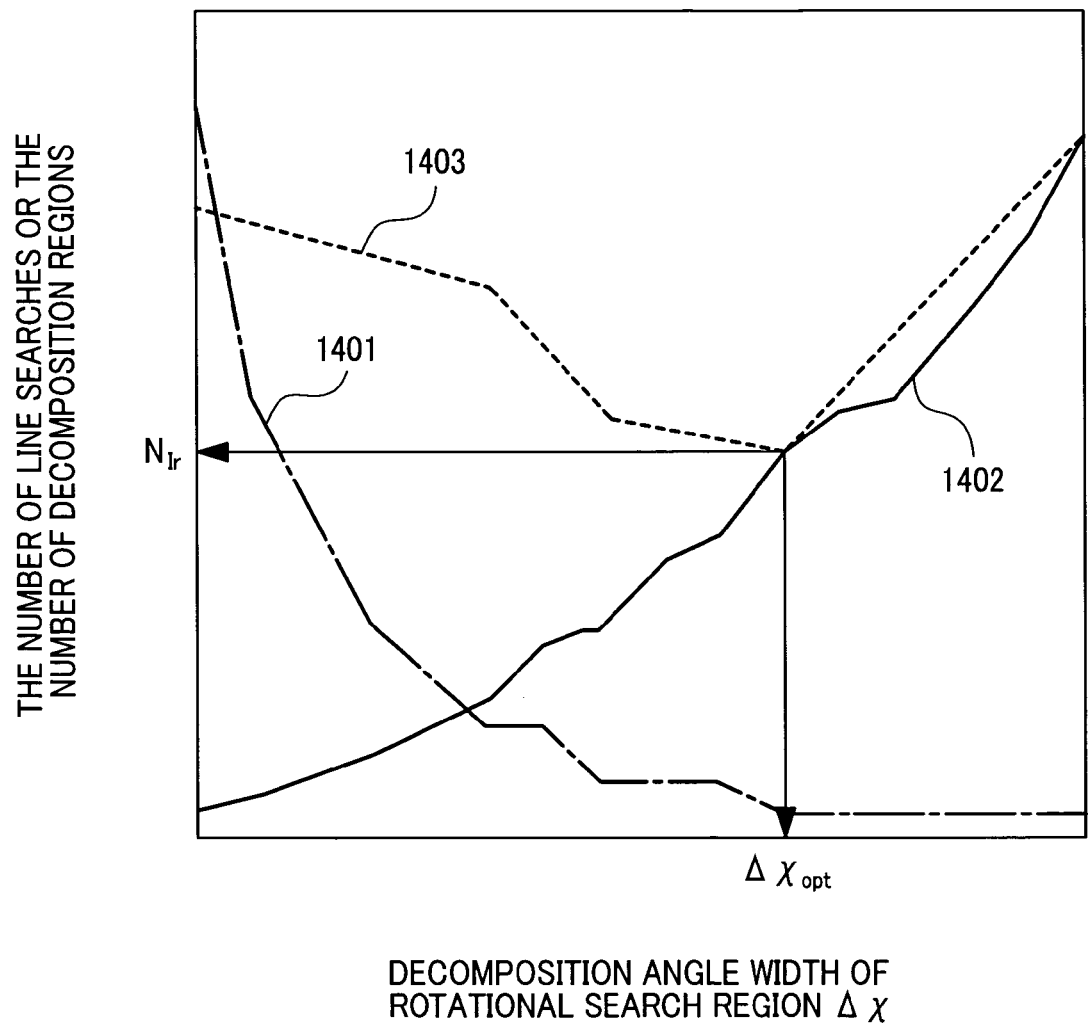
FIG. 14 is a diagram showing a change in decomposed rotational regions (hereinafter referred to as "decomposed rotational regions") that are averagely allocated to the respective computing units with respect to the decomposition angle width, a change in the number of line searches with respect to the decomposition angle width, a change in the number of line searches of the local minimum value of the binding energy with respect to the respective decomposed rotational regions with respect to the decomposed angle width, and an optimum decomposition width with the axis of abscissa indicative of the decomposition angle width of the rotational search region and the axis of ordinate indicative of the number of line searches or the number of decomposed regions.

In Step 1221, the decomposition width that minimizes the number of linearly searching the local minimum value of the binding energy, and the number of line searches are determined in the rotational search region that performs the rotational operation of compound. FIG. 14 is a diagram showing a change 1401 in decomposed rotational regions (hereinafter referred to as "decomposed rotational regions") that are averagely allocated to the respective computing units with respect to the decomposition angle width, a change 1402 in the number of line searches with respect to the decomposition angle width, a change 1403 in the number of line searches of the local minimum value of the binding energy with respect to the respective decomposed rotational regions with respect to the decomposed angle width, and an optimum decomposition width with the axis of abscissa indicative of the decomposition angle width of the rotational search region and the axis of ordinate indicative of the number of line searches or the number of decomposed regions. When the decomposition width of the rotational search region is $\Delta x$, the number of decomposition rotational regions that are averagely allocated to the respective computing units is $(x/\Delta x)^3/2N_{pa}$. Also, in the respective decomposed rotational regions, the binding energy is calculated by the line search in the energy gradient vector direction, that is, a rotational direction of the torque that is exerted on compound, and the number of line searches until the local minimum value of the binding energy is found is given by F(X) represented in Expression (3).

In this expression, $X=\Delta W/R_r$. When $R_r$ is within a distance of the radius $R_r$ from a coordinate position at which the minimum value of the binding energy exists in the decomposed rotational region, the binding energy is an energy region of a quadratic function with respect to a distance, and when $R_r$ is equal to or higher than the radius $R_r$, the binding energy is a random energy region. The number of line search 1403 of the local minimum value of the binding energy on the respective computing units is represented by their product $(x/\Delta x)^3/2N_{pa} \times F(\Delta x/R_r)$. Accordingly, when the decomposition width $\Delta_{xopt}$ where $(x/\Delta x)^3/2N_{pa} \times F(\Delta x/R_r)$ becomes the minimum is selected, the decomposition width $\Delta x_{opt}$ of the rotational search region x, as well as the binding energy on the respective computing units are calculated, thereby making it possible to determine $N_{Ir}=F(\Delta x_{opt}/R_r)$ where the number of line searches of the local minimum value of the binding energy becomes the minimum.

In Step 1222, the number of decomposition of the rotational search region and the range of the decomposed rotational regions are determined by the aid of the decomposition width $\Delta x_{opt}$ of the rotational search region x. The number of rotational regions that decompose the rotational search region x is $N_x=(x/\Delta x_{opt})^3/2$. When the rotational coordinates within the decomposed rotational region are (F, θ, ψ), $0=F=\Delta x_{opt}$, $0=θ=\Delta x_{opt}$, and $0=ψ=\Delta x_{opt}$ are set as the decomposed rotary region $x_1$, $0=F=\Delta x_{opt}$, $0=θ=\Delta x_{opt}$, and $x_{opt}=ψ=2x_{opt}$ are set as the decomposed rotary region $x_2$, ..., and $(x-\Delta x_{opt})=F=x$, $(x/2-\Delta x_{opt})=θ=x/2$, and $(x-\Delta x_{opt})=ψ=x$ are set as the decomposed rotary region $X_{Nx}$.

In general, the decomposed rotational region $x_n$ is represented by $(n_F-1)\Delta x_{opt}=F=n_F\Delta x_{opt}$, $(n_θ-1)\Delta x_{opt}=θ=n_{θ\Delta xopt}$, and $(n_θ-1)\Delta x_{opt}=ψ=n_ψ\Delta x_{opt}$, where $n=1, 2, \ldots, N_x$, $n_F$, $n_ψ=1$, $2, \ldots, x/\Delta x_{opt}$, and $n_θ=1, 2, \ldots, x/2\Delta x_{opt}$. As described above, it is possible to determine the number of decomposed rotational regions $N_x$, as well as the range of the decomposed rotational regions $x_1, x_2, \ldots, x_n, \ldots$, and $x_{Nx}$ can be determined.

In Step 1223, the number of computing units in the parallel and distributed environment where the decomposed rotational regions are allocated is determined by using the number of decomposed rotational regions $N_x$. In the case where the number of decomposed rotational regions $N_x$ is larger than the number of available computing units $N_{pa}$, the number of computing units $N_p$ to which the decomposed rotational regions are allocated is $N_{pa}$. On the other hand, in the case where the number of decomposed rotational regions $N_x$ is smaller than the number of available computing units $N_{pa}$, the number of computing units $N_p$ to which the decomposed translational regions are allocated is $N_x$. In this way, the number of computing units $N_p$ in the parallel and distributed environment for allocation of the decomposed translational regions can be determined.

In Step 1224, the number of decomposed rotational regions that are allocated to the respective computing units, and the decomposed rotational region are determined by the aid of the number of decomposed rotational regions $N_x$, the number of line searches $N_{Ir}$ as well as the number of computing units $N_p$ in the parallel and distributed environment for allocation of the decomposed rotational regions. Since the number of line searches with respect to the respective decomposed rotational regions is $N_{Ir}$, the number of decomposed rotational regions that are allocated to the respective computing units can be substantially equalized, and the number $N_{dr}$ of allocated decomposed translational regions is $[N_x/N_p]$ or $[N_x/N_p]-1$. In this expression, a value obtained in the form of [**] is rounded out to the whole number, and $N_{dr}$ decomposed rotational regions that are arbitrarily selected from the decomposed translational regions $x_1, x_2, \ldots, x_{Nx}$ are allocated to each of the $N_p$ computing units under the parallel and distributed environment.

In Step 1225, the search point within the decomposed rotational region where the binding energy is to be computed is determined in the decomposed rotational regions $x_n$ that are allocated to the computing units. It is assumed that one of search points within the decomposed translational region $x_n$ is $(F_n, θ_n, ψ_n)$. At the search point, it is assumed that the norm of a gradient vector with respect to the rotational coordinates of the binding energy is $F=(F_F, F_θ, F_ψ)$. Then, $F=(F_F, F_θ, F_ψ)$ can be obtained from $R(F_n+F_F)$, $θ_n+F_θ$, $ψ_n+F_ψ)=T (T_x, T_y, T_z) R (F_n, θ_n, ψ_n)$ by the aid of the torque vector $T=(T_x, T_y, T_z)$. In this example, R is an Euler's matrix, T is the rotational matrix of the torque. The search point within the decomposed rotational region for computing the binding energy is given by $(F_n \pm kF_F dx, θ_n \pm kF_θ dx, ψ_n \pm kF_ψ dx)$. In this expression, k is an integer that satisfies $(n_F-1)\Delta x_{opt}=F_n \pm kF_F dx=n_F\Delta x_{opt}$, $(n_θ-1)\Delta x_{opt}=θ_n \pm kF_θ dx=n_θ\Delta x_{opt}$, and $(n_ψ-1)\Delta x_{opt}=ψ_n kF_ψ dx=n_{θ\Delta xopt}$. Also, dx is the rotational width in the line search. Further, the rotational width dx can be prepared at the system side as default, or can be set through the input system 101 by the user.

As described above, when it is assumed that the number of search points is $N_{Ir,n}$, $N_{Ir,n}$ search points $(F_n \pm kF_F dx, θ_n \pm kF_θ dx, ψ_n \pm kF_ψ dx)$ within the decomposed rotational regions where the binding energy is to be computed can be determined with respect to the decomposed rotational regions $x_n$ that have been allocated to the respective computing units.

In the communication control of Step 1226, data of the search points that are allocated in order to compute the binding energy by the respective computing units which are determined in Step 1224 and Step 1225 is transmitted. When it is assumed that the decomposed rotational regions $x_n$ are allocated to the computing units $P_m$ in Step 1224, and $N_{Ir,n}$ search points $(F_n \pm kF_F dx, θ_n \pm kF_θ dx, ψ_n \pm kF_ψ dx)$ which exist within the decomposed rotational region $x_n$ are given in Step 1225, $N_{Ir,n}$ search points $(F_n \pm kF_F dx, θ_n \pm kF_θ dx$ and $ψ_n \pm kF_ψ dx)$ are transmitted to the computing unit $P_m$. In this way, data of $N_{Ir,n}$ search points $(F_n \pm kF_F dx, θ_n \pm kF_θ dx,$ and $ψ_n \pm kF_ψ dx)$ that exist within the decomposed rotational regions $x_n$ which are allocated to the respective computing units are transmitted to all of the computing units $P_1, P_2, \ldots, P_{Np}$. On the contrary, the binding energies at the search points which have been computed by the respective computing units and the gradient vectors of the binding energy with respect to the rotational coordinate, that is, a force that is exerted on compound is received. The binding energy of compound that has been subjected to rotational operation and protein in water molecule, and a force that is exerted on compound are received with respect to $N_{Ir,n}$ rotational coordinates $(F_n \pm kF_F dx, θ_n \pm kF_θ dx,$ and $ψ_n \pm kF_ψ dx)$ which exist within the decomposed rotational regions $x_n$ which have been transmitted to the computing units $P_m$.

In Step 1227, the minimum value is determined from the local minimum values of the binding energies that have been received in Step 1226 and computed by the respective computing units and the local minimum value that has been computed by all of the computing units. The search point that gives the smallest binding energy in $N_{Ir,n}$ binding energies is selected in correspondence with the $N_{Ir,n}$ search points $(F_n \pm kF_F dx, θ_n \pm kF_θ dx,$ and $ψ_n \pm kF_ψ dx)$ which exist within the decomposed rotational regions $x_n$ which have been computed by the computing units $P_m$. The line search repeats the iterative calculation that is $N_{lr}$ times or more in the number of line searches. The selected search point is a search point at which the gradient vector of the binding energy is obtained with respect to the rotational coordinates described in Step 1225. The binding energy that has been obtained as the result of the iterative calculation is the local minimum value of the binding energies within the decomposed rotational regions $x_n$. Then, the smallest energy among the local minimum values of the binding energies that have been obtained in correspondence with all of the computing units $P_1, P_2, \ldots, P_{Nx}$ is the minimum value of the binding energy.

In Step 1228, it is determined whether the iterative calculation of the line search is repeated, or not, on the basis of the convergence of the local minimum values of the binding energy within the decomposed rotational region. When the number of line searches of the decomposed translational region $x_n$ which have been allocated to the computing units $P_n$ is $N_{lr}$ or lower, control is returned to Step 1225, and the iterative calculation of the line search is executed. When the number of line searches of the decomposed rotational region $x_n$ which have been allocated to the computing units $P_n$ is equal to or higher than $N_{lr}$, or when a difference between the local minimum value of the binding energy and the local minimum value of the binding energy which has been found in the previous iterative calculation is converged to a threshold energy or lower, the line search is completed. The minimum value of the binding energy of protein and compound in water molecule, as well as the atomic coordinate data with respect to the binding structure of protein and compound in water molecule is transmitted to the output system 103.

In Step 1229, data at the search points from Step 1226 is received in the computing unit of the parallel and distributed computer system. The respective computing units $P_m$ receive $N_{lr,n}$ rotational coordinates ($F_n \pm kF_F dx$, $\theta_n \pm kF_\theta dx$, and $\psi_n \pm kF_\psi dx$) within the decomposed rotational regions $x_n$. The respective computing units $P_m$ execute the rotational operation with respect to the atomic coordinates of compound by using the search points ($F_n \pm kF_F dx$, $\theta_n \pm kF_\theta dx$, and $\psi_n \pm kF_\psi dx$). The respective computing units $P_m$ computes $N_{lr,n}$ binding energies and a torque that is exerted on compound on the basis of the atomic coordinates of compound and protein that have been subjected to rotational operation. The binding energies corresponding to $N_{lr,n}$ search points ($F_n \pm kF_F dx$, $\theta_n \pm kF_\theta dx$, and $\psi_n \pm kF_\psi dx$) which exist within the decomposed rotational regions $X_n$, and the torque that is exerted on compound are transmitted to Step 1226.

Figure 15:
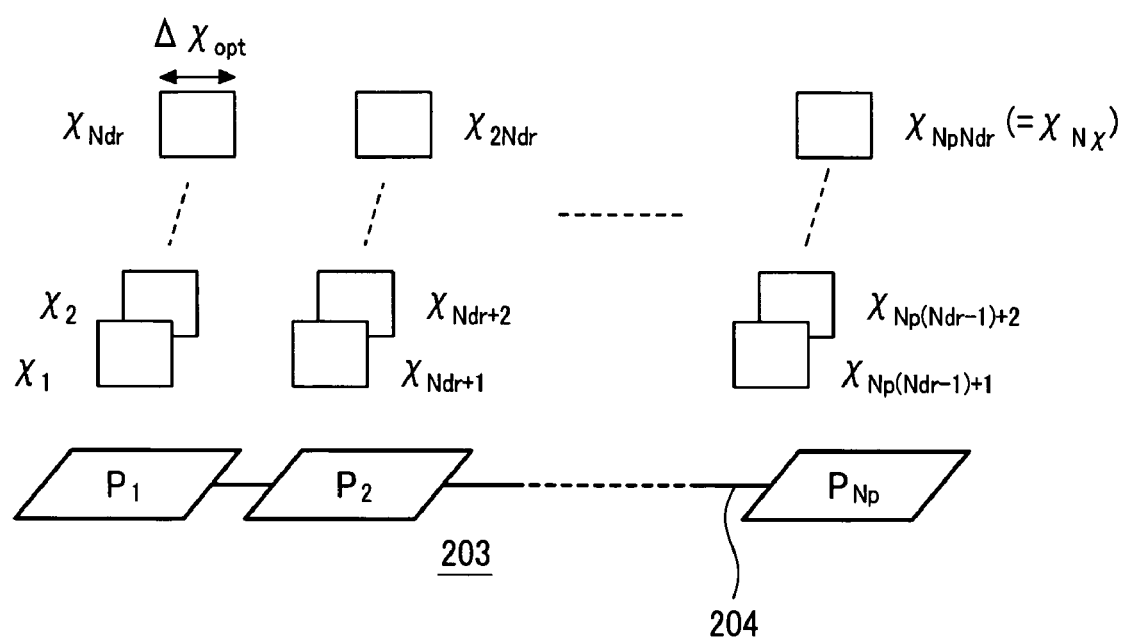
FIG. 15 is a diagram showing an example in which the decomposed rotational regions are allocated to the computing units of the computing unit groups that are connected to each other on the network.

FIG. 15 is a diagram showing an appearance in which the decomposed rotational regions $x_1, x_2, \ldots, x_{Ndr}$ are allocated to the computing unit $P_1$ in the computing unit group 203 that is connected on the network 204, the decomposed rotational regions $x_{Ndr+1}, x_{Ndr+2}, \ldots, x_{2Ndr}$ are allocated to the computing unit $P_2, \ldots$, and the decomposed rotational regions $x_{Np(Ndr-1)+1}, X_{Np(Ndr-1)+2}, \ldots, x_{NpNdr}(=x_{Nx})$ are allocated to the computing unit $P_{Np}$. The range of the decomposed translational region $x_n$ that is allocated to the computing unit $P_m$ is $(n_F-1)\Delta x_{opt}=F=n_F \Delta x_{opt}$, $(n_\theta-1)\Delta x_{opt}=\theta=n_\theta \Delta x_{opt}$, and $(n_\psi-1)\Delta x_{opt}=\psi=n_\psi \Delta x_{opt}$, where $m=1, 2, \ldots, N_p$, $n=1, 2, \ldots$, and $N_x, n_F, n_\psi=1, 2, \ldots, x/\Delta x_{opt}$, and $n_\theta=1, 2, \ldots, x/2\Delta x_{opt}$.

Figure 16:
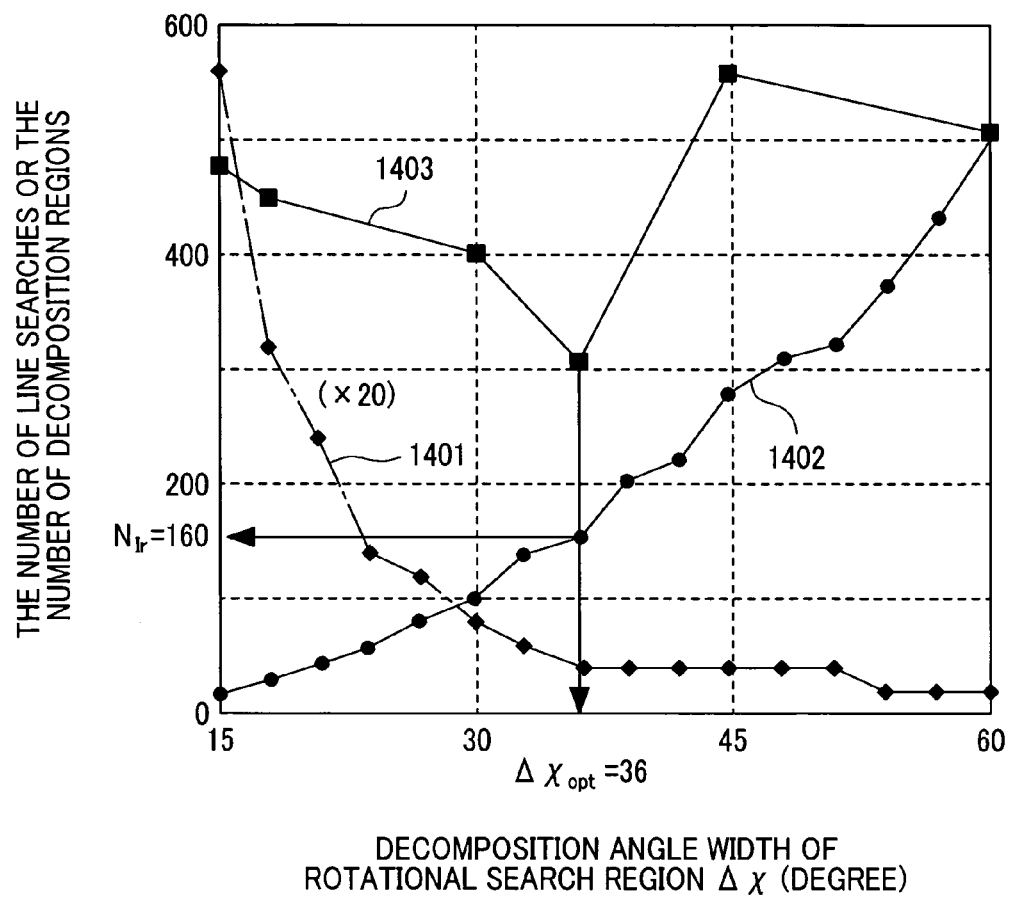
FIG. 16 is a diagram showing a change in decomposed rotational regions (hereinafter referred to as "decomposed rotational regions") that are averagely allocated to the respective computing units with respect to the decomposition angle width, a change in the number of line searches with respect to the decomposition angle width, a change in the number of line searches of the local minimum value of the binding energy with respect to the respective decomposed rotational regions with respect to the decomposed angle width, and an optimum decomposition width with the axis of abscissa indicative of the decomposition angle width of the translational search region and the axis of ordinate indicative of the number of line searches or the number of decomposed regions.

Referring to FIG. 16, a description will be given of a specific example in which the angle region width $x=360°$ of the rotational search region is inputted from the input system 101, and the number of available computing units $N_{pa}=250$ in the parallel and distributed computer system is inputted as the search region with respect to the binding structure of protein and compound in water molecule. In Step 1221, the number of decomposed rotational regions on the respective computing units with respect to the decomposition width of the rotational search region, the number of line searches in order to obtain the local minimum value of the binding energy in the decomposed rotational region, as well as the number of line searches that obtain the local minimum value of the binding energy on the respective computing units are determined. FIG. 16 is a diagram showing a change 1401 in the decomposed transactional regions (hereinafter referred to as "decomposed translational region") that are averagely allocated to the respective computing units with respect to the decomposition width, a change 1402 in the number of line searches of the local minimum value of the binding energy with respect to the decomposition width in the respective decomposed translational regions when $R_r$ is 15°, as well as a change 1403 in the number of line searches that obtain the local minimum value of the binding energy on the respective computing units, and an optimum decomposition angle width with the axis of abscissa indicative of the decomposition angle width (degree) of the rotational search region and the axis of ordinate indicative of the number of line searches or the number of decomposed regions. It can be obtained that the decomposition width $\Delta x_{opt}$ of the rotational search region which minimizes the number of line searches on the respective computing units is 36°, and the number of line searches $N_{lr}$ is 160.

Figure 17:
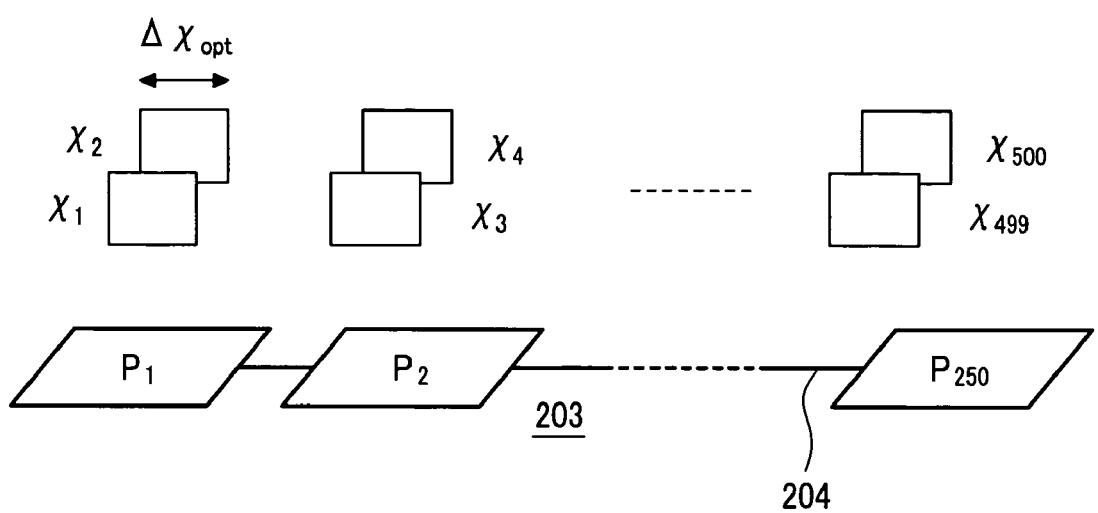
FIG. 17 is a diagram showing an example in which the decomposed rotational regions that minimize the number of line searches are allocated to the computing units of the computing unit groups that are connected to each other on the network.

In Step 1222, the number of decomposed rotational regions is 500 because of $N_x=(x/\Delta x_{opt})^3/2$ by the aid of the optimum decomposition width $\Delta x_{opt}=36°$. In Step 1223, since the number of decomposed regions $N_x=500$ is larger than the number of available computing units $N_{pa}=250$, the number of computing units $N_p$ to which the decomposed rotational regions are to be allocated is 250. In Step 1224, since the number of line searches $N_{lr}$ with respect to the respective decomposed rotational regions is 160, the number of decomposed rotational regions that are allocated to the respective computing units can be substantially equalized. For example, as shown in FIG. 17, the number of decomposed rotational regions $N_{dr}$ that are allocated to the respective computing units is distributed as 2 with respect to the number of computing units $N_p=250$. In Step 1225, the search points of the line searches within the decomposed rotational region which are allocated to the respective computing units are determined. In Step 1226, data at the search points of the line searches is transmitted to the respective computing units, and in Step 1229, the binding energy corresponding to the search point in the respective computing units, and the gradient vector of the binding energy with respect to the rotational coordinates are computed, and transmitted to Step 1226. In Step 1227, the local minimum value of the binding energy which has been computed by the respective computing units is obtained. In Step 1228, the iterative calculation that is 160 or more in the number of line searches $N_{lr}$ is executed.

Figure 18:
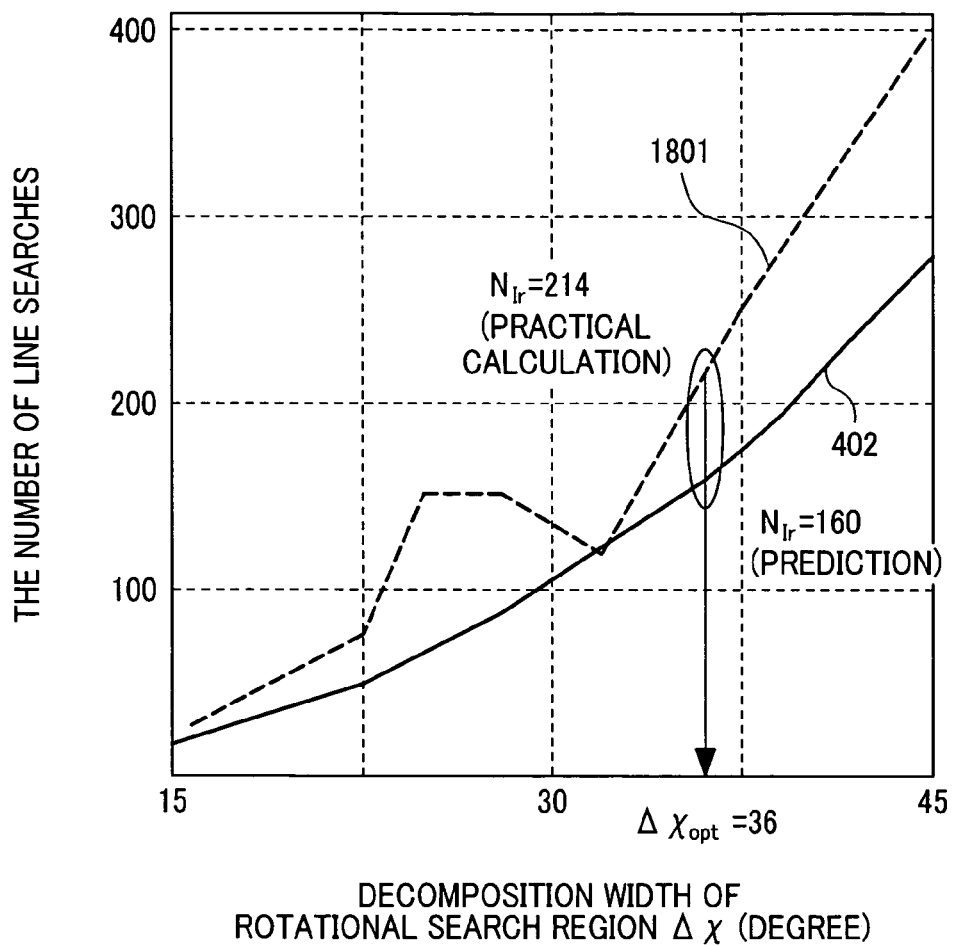
FIG. 18 is a diagram showing the number of line searches that obtains the local minimum value of the binding energy with respect to the decomposition width of the decomposed rotational regions.

FIG. 18 is a diagram showing the number of line searches that obtain the local minimum values of the binding energy. A solid line 402 represents a predicted value that is obtained in Step 1221, and a dotted line 1801 is the computation results of the simulation. In the simulation, the average number of line searches that obtain the local minimum value of the binding energy in the decomposed rotational region is 214, which relatively excellently coincides with the predicted value. The number of line searches on the respective computing units is a product of the number of line searches of the respective decomposed rotational regions and the number of decomposed regions on the respective computing units, and therefore 320.

On the other hand, the number of line searches for obtaining the local minimum value of the binding energy when only one of the computing units is used is predicted as 9612 by the aid of Expressions (3) to (20). Therefore, the number of line searches that obtain the local minimum values of the binding energy is reduced down to $9612/320=1/30$ times by means of the design system of a binding structure for polymer molecule using the parallel and distributed computer system, thereby making it possible to compute the binding structure that minimizes the binding energy in a high speed. In other words, the user is capable of performing high-speed computation by merely setting the angle region width that represents a range of the rotational search region of the atomic coordinates of polymer molecule to be subjected to simulation, and the number of available computing units $N_{pa}$ in the parallel computers or the PC cluster under the parallel and distributed environment.

What is claimed is:

1. A design system of a binding structure for polymer molecule which is executed by a parallel and distributed computer system, the parallel and distributed computer system, comprising:

a plurality of computing units including a CPU that executes computing, a memory system that holds necessary program and data, an input/output interface, and a bus that connects the CPU, the memory system, and the input/output interface;

a personal computer including an input system that inputs necessary data by a user, a transaction and control unit, an output system that outputs data for the user, a memory system that holds necessary program and data, an input/output interface, and a bus that connects the input system, the output system, the memory system, and the input/output interface, and executing a transaction for distributing computation to the plurality of computing units and integrating the computation result of the plurality of computing units; and a network that executes data transfer between the personal computer and the computing units through the input/output interface, wherein the transaction and control unit of the personal computer executes a transaction procedure of distributing computation to the respective computing units and integrating the computation results of the respective computing units with respect to the number of operable computing units that are designated by the user, and the search region of polymer molecule, and wherein the transaction procedure comprises the steps of:

(1) determining a decomposition width that decomposes a search region and the number of searches that compute a binding energy;

(2) determining the number of decomposed search regions (decomposed regions) and a range of the decomposed regions by using the decomposition width of the search region;

(3) determining the number of computing units in the parallel and distributed environment for allocation of the decomposed regions within the number of operable computing units by using the number of decomposed regions;

(4) determining the number of decomposed regions that are allocated to each of the respective computing units and which of the decomposed regions are assigned to the respective computing units by using the number of decomposed regions, the number of searches, and the number of computing units to which the decomposed regions are allocated;

(5) determining the search points within the decomposed regions where the binding energy is computed in the decomposed regions that are allocated to the respective computing units;

(6) transmitting data at the respective search points which are allocated in order to compute the binding energy to the respective computing units that are determined in the steps (4) and (5), and receiving the binding energies and the energy gradient vector at the respective search points which are computed by the respective computing units for communication control;

(7) determining the minimum value in the local minimum values of the binding energies that are computed by the respective computing units which are received in the step (6), and the local minimum value that is computed by all of the computing units;

(8) determining whether iterative calculation is executed, or not, on the basis of the convergence of the local minimum value of the binding energy within the decomposed region, or denies the iterative calculation when the number of searches exceeds a given value; and (9) returning the control to the step (5) in the case where the iterative calculation is executed, and outputting data of the atomic coordinates with respect to the minimum value of the binding energy of polymer molecule and the binding structure of polymer molecule to the output system in the case where the iterative calculation is completed, wherein the transaction in the respective computing units includes a step of receiving data at the search points from the step (6), and computing the binding energy of polymer molecule and the energy gradient vector at the designated search point.

2. The design system of a binding structure for polymer molecule according to claim 1, wherein the transaction procedures of distributing the computation to the respective computing units and integrating the computation results of the respective computing units among the functions of the personal computers are shared to one of the computing units.

3. The design system of a binding structure for polymer molecule according to claim 1, wherein the personal computer and the computing units are formed of a single computer.

4. The design system of a binding structure for polymer molecule according to claim 1, wherein the network includes a management unit of a parallel and distributed computer system that collects the number of operable computing units among the computing units, the transaction performance of the operable computing units, and the information on the network speed, and supplies the information to the personal computer.

5. The design system of a binding structure for polymer molecule according to claim 1, wherein the step of determining the number of searches which computes the decomposition width that decomposes the search region and the binding energy selects a decomposition width $\Delta W_{opt}$ that minimizes a product of the number of decomposed translational regions that are averagely allocated to the respective computing units according to the decomposition width that decomposes the search region, and the number of line searches of the local minimum values of the binding energy in the decomposed translational region as the decomposition width, and selects the number of searches in the decomposition width as the number of searches minimizes a product of the number of decomposed translational or rotational regions that are averagely allocated to the respective computing units according to the decomposition width that decomposes the search region, and the number of line searches of the local minimum values of the binding energy in the decomposed translational or rotational region as the decomposition width, and selects the number of searches in the decomposition width as the number of searches.

6. The design system of a binding structure for polymer molecule according to claim 5, wherein a prediction of the number of searches in the decomposed region using the decomposition width of the search region has, as a predicted value of the number of searches, the number of line searches until the binding energy is computed at the search points on a line in a direction of the energy gradient vector, the computation of the energy gradient vector is repeated at the search points on the line which minimize the binding energy, and the local minimum value of the binding energy is obtained.

7. The design system of a binding structure for polymer molecule according to claim 6, wherein the number of line searches determines the number of searches of decomposed regions which is predicted by using the decomposition width of the search region, and a distance of the energy region which is a quadratic function with respect to a distance from the local minimum position of the binding energy.

8. The design system of a binding structure for polymer molecule according to claim 7, wherein the size of a radius $R_f$ is prepared at the system side as default, or is designated by the user, in the energy region where binding energy from a coordinate position at which the minimum value of the binding energy exits is a quadratic function with respect to a distance.

9. The design system of a binding structure for polymer molecule according to claim 5, wherein when the number of decomposed regions is smaller than the number of available computing units which is inputted from the input system by the user, the number of decomposed regions is set as the number of computing units to which the decomposed regions are to be allocated, and when the number of decomposed regions is larger than the number of available computing units which is inputted from the input system by the user, the number of computing units to which the decomposed regions are to be allocated is set to the number of operable computing units.

10. The design system of a binding structure for polymer molecule according to claim 9, wherein the number of operable computing units is data that is given from the management unit of the parallel and distributed computer system which is disposed in the system, or a value that is determined by the user with reference to the data given from the management unit.

11. The design system of a binding structure for polymer molecule according to claim 9, wherein the number of decomposed regions that are allocated to the respective computing units and a range of the decomposed region are determined according to the number of decomposed regions that is set according to the number of operable computing units, the number of searches of the decomposed regions, and the number of computing units to which the decomposed regions are to be allocated.

12. The design system of a binding structure for polymer molecule according to claim 4, wherein the number of computing units having the transaction performance converted to the identical transaction performance is deviated from the number of operable computing units and the transaction performance of the operable computing units which are supplied from the management unit of the parallel and distributed computer system to determine the number of decomposed regions that are allocated to the respective computing units, and a range of the decomposed regions.

13. The design system of a binding structure for polymer molecule according to claim 1, wherein, in the decomposed regions that are allocated to the respective computing units, a gradient vector with respect to the binding energy is computed at one point of search points that exist within the decomposed regions, and a search point that exists on a line in a direction of the gradient vector and at which the binding energy that exists within the decomposed region is to be computed is set.

14. The design system of a binding structure for polymer molecule according to claim 1, wherein data related to the decomposed regions that are allocated to the respective computing units and the search points that exist within the decomposed regions and compute the binding energy is transmitted to the computing unit that computes the binding energy and the energy gradient vector on the parallel and distributed computer system, whereas the binding energy and the energy gradient vector at the search points that are computed by the respective computing units are received.

15. The design system of a binding structure for polymer molecule according to claim 1, wherein the respective computing units determine the minimum value from the local minimum value of the binding energy that is computed in correspondence with the search points within the decomposed regions, and the local minimum values that are computed by all of the computing units.

16. The design system of a binding structure for polymer molecule according to claim 1, wherein in the transaction and control unit, said step (5) through said step (7) are executed by the iterative calculations having the predicted number of searches of the decomposed regions, or more, and the iterative calculation is executed until a difference between the local minimum values of the binding energy and the minimum values of the binding energy which is obtained in a previous iterative calculation is converged to a threshold energy or lower.

17. The design system of a binding structure for polymer molecule according to claim 1, wherein each of the computing units receives the search points within the decomposed regions which are allocated to the respective computing units through the communication control step of the transaction and control unit of the personal computer, performs the translational operation and the rotational operation with respect to the position of polymer molecule, computes the binding energy and the energy gradient vector with respect to the atomic coordinates of polymer molecule that performs the translational operation and the rotational operation, and transmits the computation results of the binding energy and the energy gradient vector to the transaction and control unit of the personal computer through the communication control step.

18. The design system of a binding structure for polymer molecule according to claim 1, wherein the user inputs the search region of the translational operation with respect to compound and the rotational operation with respect to compound for a binding structure of protein and compound in water molecule as the binding structure of polymer molecule through the input system of the personal computer.

19. The design system of a binding structure for polymer molecule according to claim 18, wherein a force that is exerted on polymer molecule at the search point is computed with respect to the translational operation, and a torque that is exerted on polymer molecule at the search point is computed with respect to the rotational operation, as the energy gradient vector.

20. The design system of a binding structure for polymer molecule according to claim 18, wherein the translational width dw of the translational operation and the decomposed angle width of the rotational operation in the computation of the energy gradient vector are prepared at the system side as default, or can be designated by the user through the input system.

* * * * *

UNITED STATES PATENT AND TRADEMARK OFFICE
CERTIFICATE OF CORRECTION

PATENT NO.         : 8,145,432 B2
APPLICATION NO.    : 11/657090
DATED              : March 27, 2012
INVENTOR(S)        : Ho It is certified that error appears in the above-identified patent and that said Letters Patent is hereby corrected as shown below:

On the Title Page, Item (54) and Column 1, title, delete
"System of Binding Structure for Polymer Molecule"

and insert
--Design System of Binding Structure for Polymer Molecule--

Signed and Sealed this
Twelfth Day of June, 2012

David J. Kappos
*Director of the United States Patent and Trademark Office*